(12) United States Patent
Yamada et al.

(10) Patent No.: US 8,085,040 B2
(45) Date of Patent: Dec. 27, 2011

(54) MAGNETIC RESONANCE IMAGING APPARATUS AND MAGNETIC RESONANCE IMAGING METHOD

(75) Inventors: Shinya Yamada, Naka-Gun (JP); Hitoshi Kanazawa, Utsunomiya (JP); Tokunori Kimura, Yaita (JP); Masaaki Umeda, Sakura (JP)

(73) Assignees: Tokai University Educational System, Shibuya-Ku, Tokyo (JP); Toshiba Medical Systems Corporation, Otawara-Shi, Tochigi (JP)

( * ) Notice: Subject to any disclaimer, the term of this patent is extended or adjusted under 35 U.S.C. 154(b) by 0 days.

(21) Appl. No.: 12/926,023

(22) Filed: Oct. 21, 2010

(65) Prior Publication Data

US 2011/0037466 A1    Feb. 17, 2011

Related U.S. Application Data

(62) Division of application No. 11/898,110, filed on Sep. 10, 2007, now Pat. No. 7,880,464.

(30) Foreign Application Priority Data

Sep. 13, 2006  (JP) ................................ 2006-248541

(51) Int. Cl.
   *G01V 3/00*    (2006.01)
(52) U.S. Cl. ........ 324/306; 324/307; 324/309; 600/413; 600/419
(58) Field of Classification Search .................. 324/306, 324/307, 309; 600/413, 419
   See application file for complete search history.

(56) References Cited

U.S. PATENT DOCUMENTS

| | | | |
|---|---|---|---|
| 6,271,665 B1 | 8/2001 | Berr et al. | |
| 6,564,080 B1 | 5/2003 | Kimura | |
| 7,412,277 B1 | 8/2008 | Saranathan et al. | |
| 7,545,142 B2 | 6/2009 | Alsop | |
| 7,587,233 B2 * | 9/2009 | Wong et al. | 600/419 |
| 7,623,901 B2 | 11/2009 | Kanazawa | |
| 7,627,360 B2 * | 12/2009 | Kimura | 600/419 |
| 7,880,464 B2 * | 2/2011 | Yamada et al. | 324/306 |

FOREIGN PATENT DOCUMENTS

JP    04-126129    4/1992
(Continued)

OTHER PUBLICATIONS

Nishimura, et al., "Considerations of Magnetic Resonance Angiography by Selective Inversion Recovery," *Magnetic Resonance in Medicine*, vol. 7, pp. 482-484 (1988).
Office Action mailed Apr. 26, 2011 in Japanese Application No. JP 2006-248541 with English translation.
(Continued)

*Primary Examiner* — Louis Arana
(74) *Attorney, Agent, or Firm* — Nixon & Vanderhye PC

(57) ABSTRACT

A magnetic resonance imaging apparatus includes an imaging unit which applies a labeling pulse to invert a spin included in a labeling region within part of a imaging region and then collects a echo signal from a time point when an inversion time has passed from the application of the labeling pulse, and a control unit, the control unit controlling the imaging unit so that the echo signal in the imaging region is collected a plurality of times with variations in the inversion time, the control unit also controlling the imaging unit so that a time ranging from a reference time point within a biological signal obtained from a subject to the application of the labeling pulse is a time determined in accordance with the inversion time.

20 Claims, 19 Drawing Sheets

FOREIGN PATENT DOCUMENTS

| | | |
|---|---|---|
| JP | 2001 252263 | 9/2001 |
| JP | 2002-143125 | 5/2002 |
| JP | 2003-225222 | 8/2003 |
| JP | 2004-024637 | 1/2004 |
| JP | 2005-305151 | 11/2005 |

OTHER PUBLICATIONS

Nakamura, K. et al., "Oxygen-enhanced ventilation MR imaging of the lung using ECG-gated half-Fourier FSE at 0.5T," Proc. Intl. Soc. Mag. Reson. Med., Apr. 2000, p. 2179.

* cited by examiner

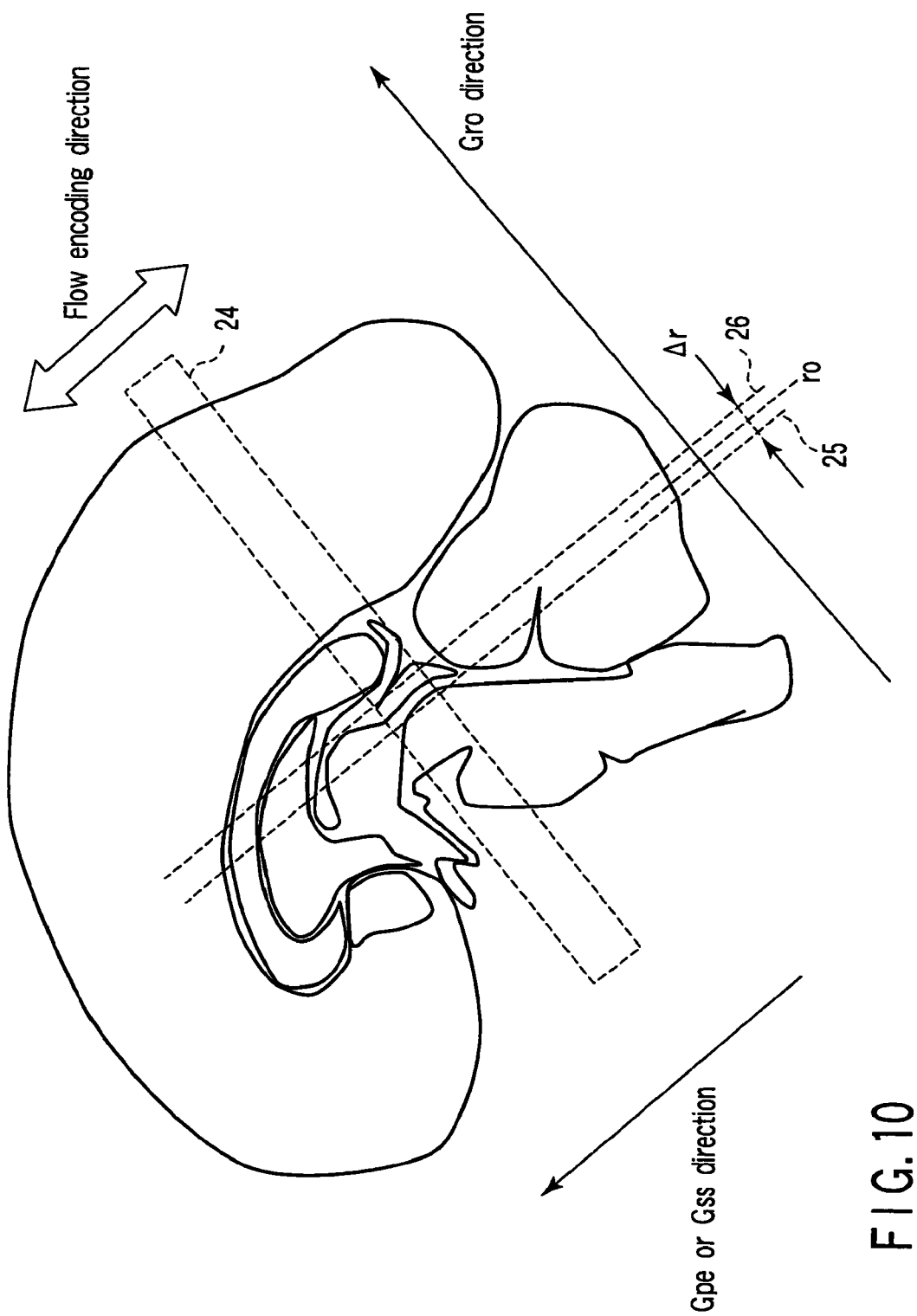
F I G. 10

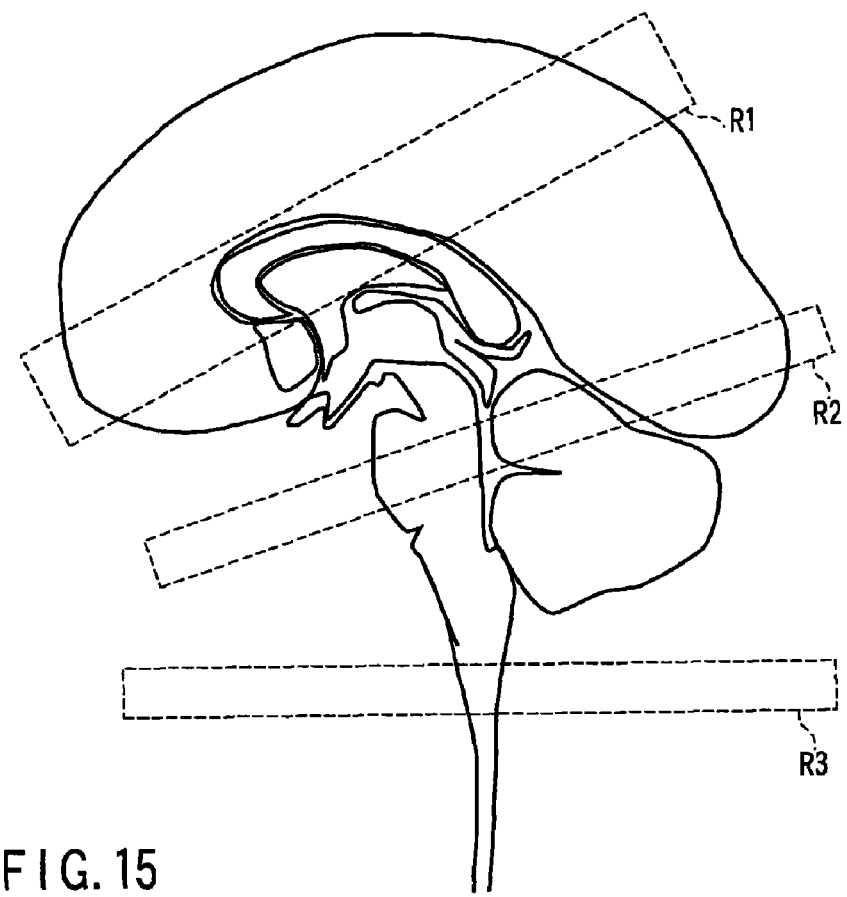
F I G. 15
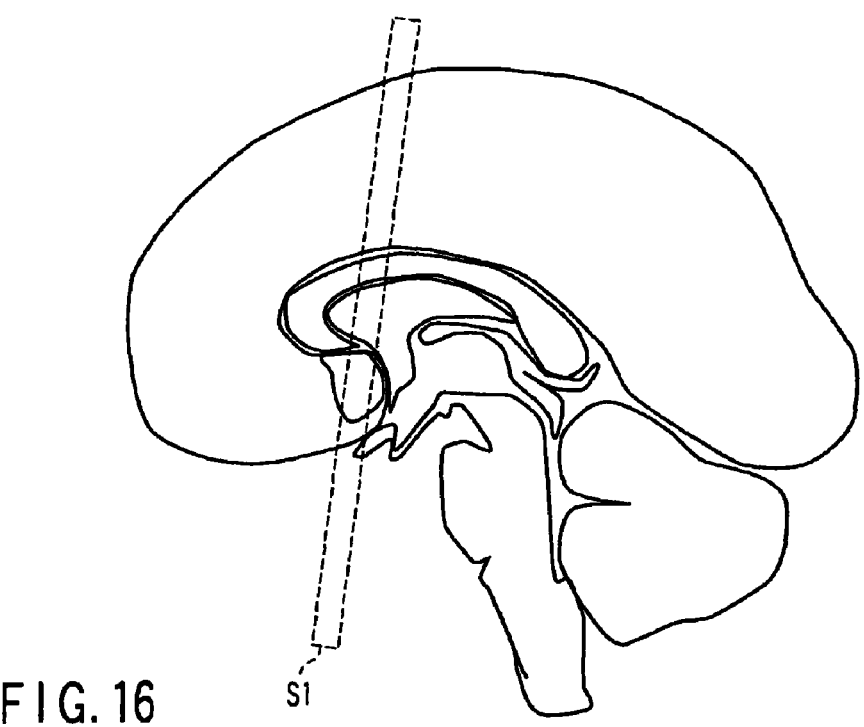
F I G. 16

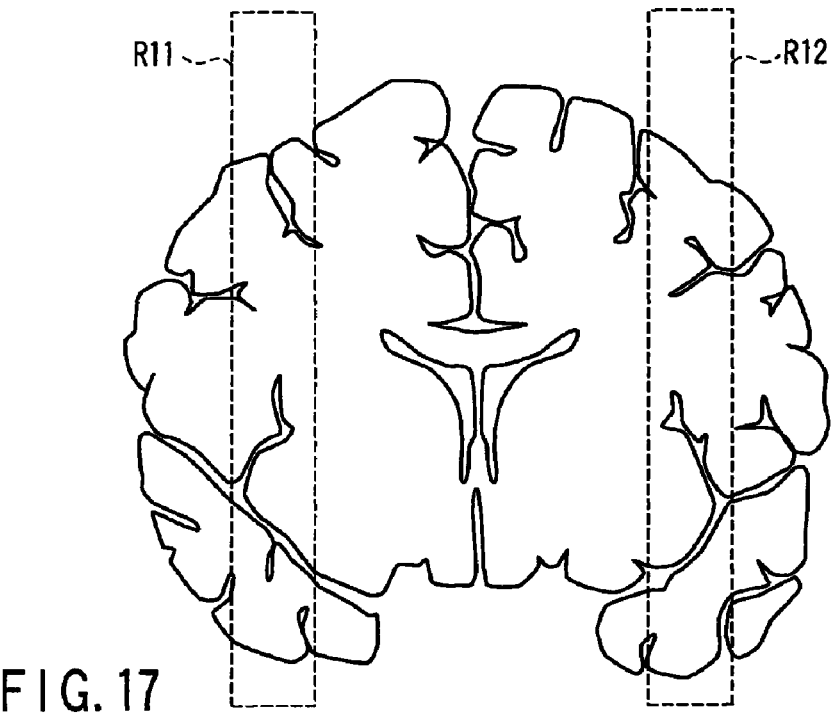
F I G. 17
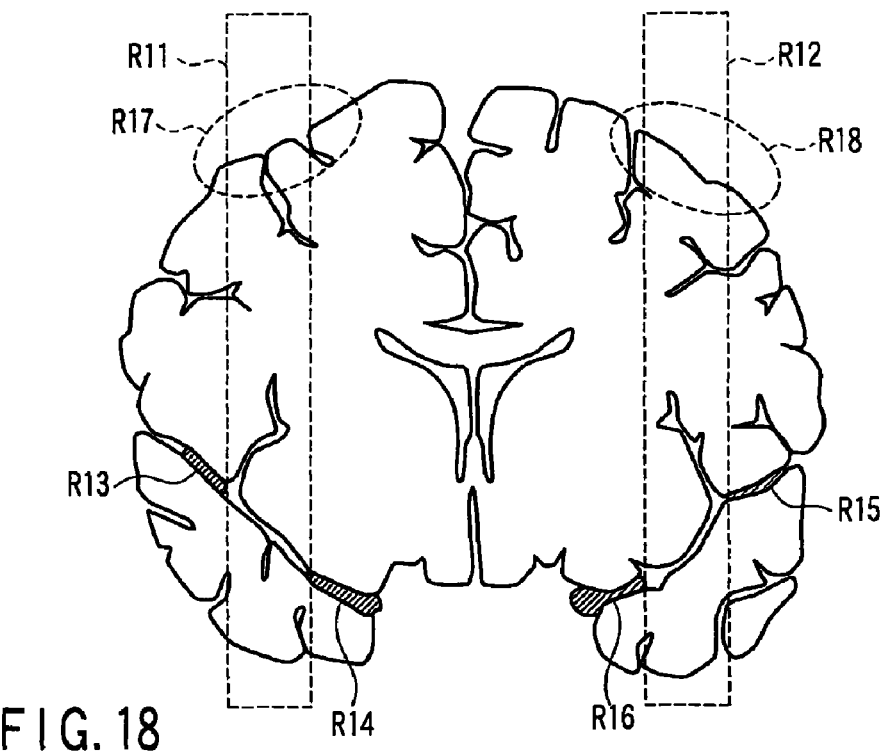
F I G. 18

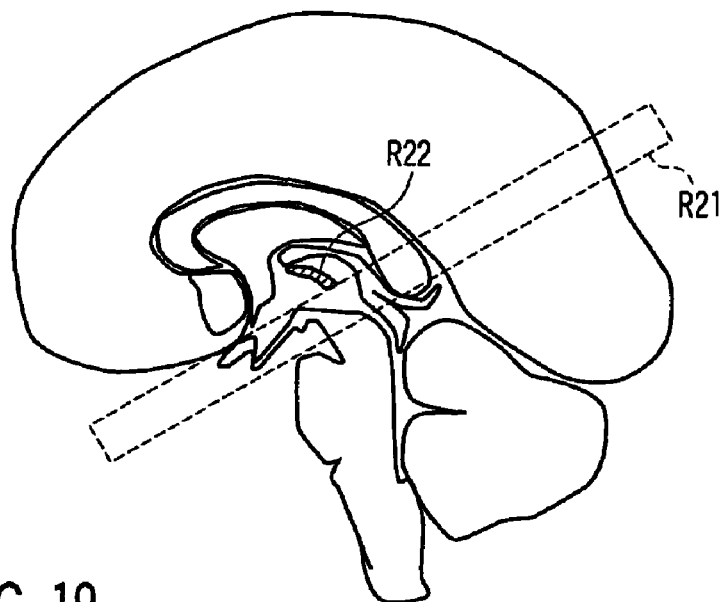
F I G. 19
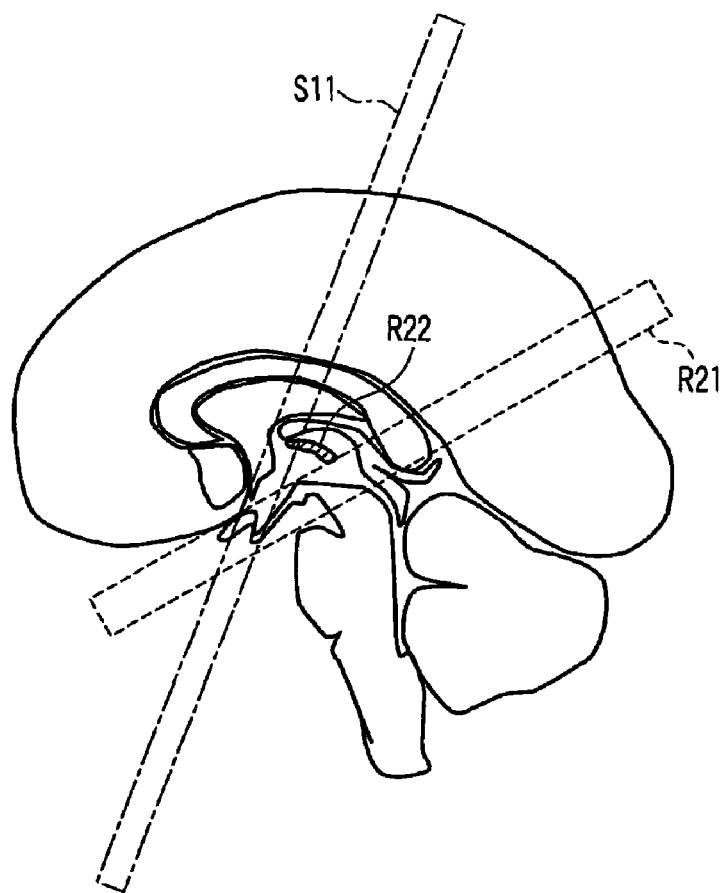
F I G. 20

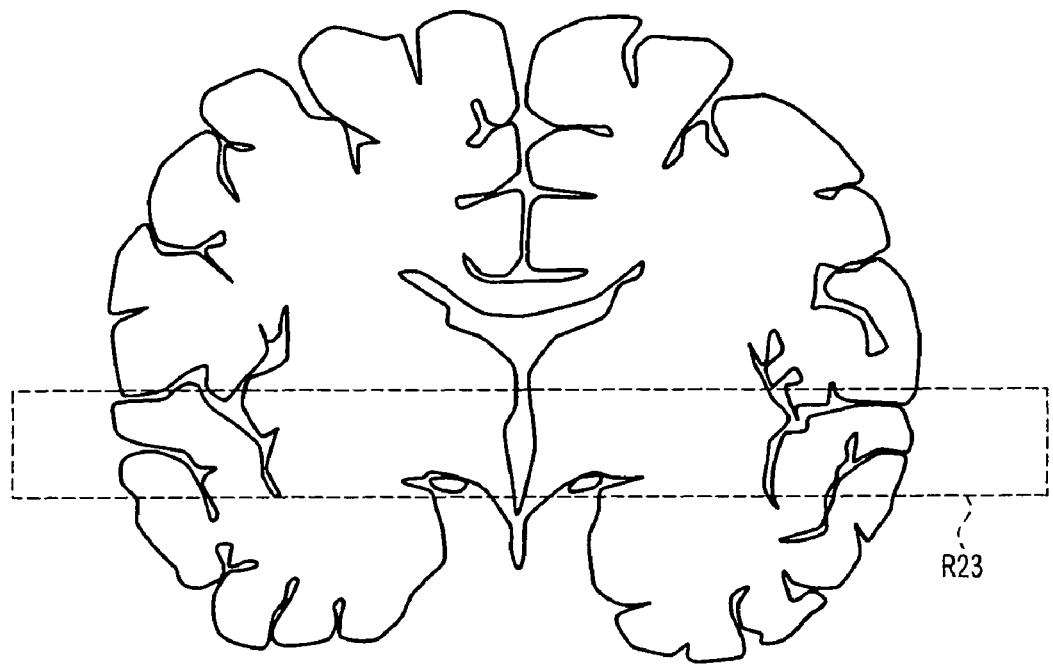
F I G. 21
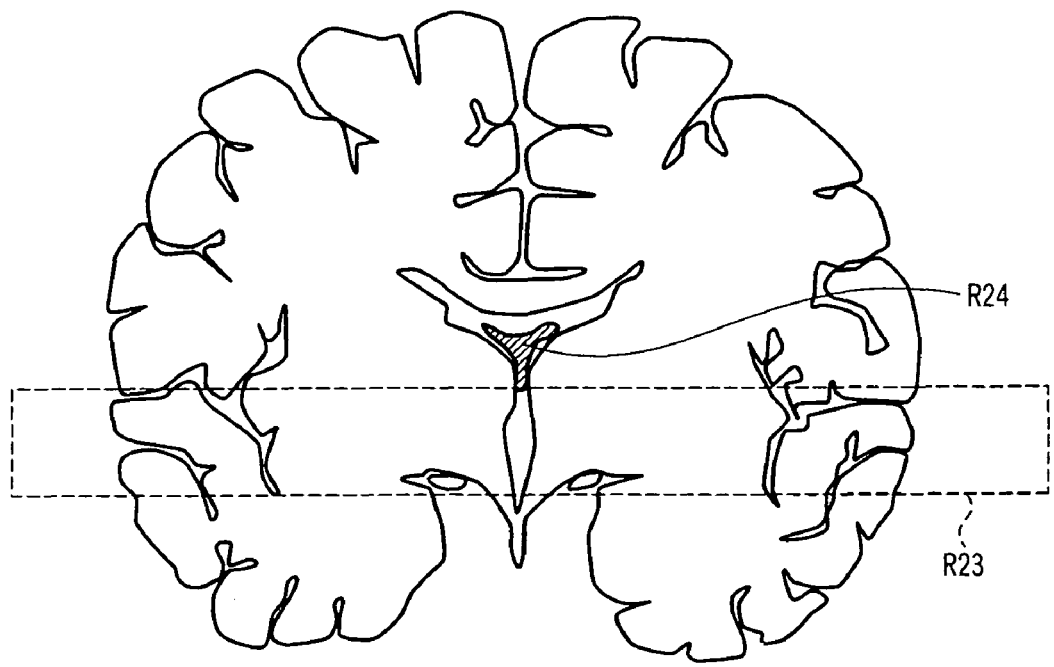
F I G. 22

MAGNETIC RESONANCE IMAGING APPARATUS AND MAGNETIC RESONANCE IMAGING METHOD

CROSS-REFERENCE TO RELATED APPLICATIONS

This application is a division of Ser. No. 11/898,110 filed Sep. 10, 2007, now U.S. Pat. No. 7,880,464, which is based upon and claims the benefit of priority from prior Japanese Patent Application No. 2006-248541, filed Sep. 13, 2006, the entire contents of both of which are incorporated herein by reference.

BACKGROUND OF THE INVENTION

1. Field of the Invention

The present invention relates to a magnetic resonance imaging apparatus and a magnetic resonance imaging method suited to an observation of the dynamic state of a moving material in a body such as blood or cerebrospinal fluid (CSF).

2. Description of the Related Art

A method has been known wherein inversion pulses are applied in order to label, in the form of longitudinal magnetization, an observation target located in a position at a time, and an MRI image is taken after a given time, thereby recognizing the distribution of the labeled observation target (e.g., refer to "Considerations of Magnetic Resonance Angiography by Selective Inversion Recovery," D. G. Nishimura et al., Magnetic Resonance in Medicine, Vol. 7, pages 472-484 (1988)).

In the case where this method is used, in general, a time when a characteristic electrocardiographic waveform such as an R wave emerges is set as a reference so that RF excitation and echo signal collection for imaging are carried out at a time when a certain amount of time has passed from the above-mentioned time. This utilizes the nature of the flow velocity change of, for example, blood or cerebrospinal fluid that often highly correlates with a cardiac phase. Such a synchronization method is employed because artifacts due to pulsation can be reduced, because the capability to visualize, for example, the blood or cerebrospinal fluid and signal strength are stabilized, and because image quality is improved.

Another method has been known that conducts labeling for longitudinal magnetization by a selective excitation method before echo signal collection for imaging, and takes a plurality of images with variations in an inversion time TI ranging from the time of the labeling to the imaging (e.g., refer to Japanese Patent Application KOKAI Publication No. 2001-252263). The plurality of images obtained by this method is sequentially displayed at regular intervals such that it is possible to observe the dynamic state of a moving material in a body such as the blood or cerebrospinal fluid.

FIG. 24 is a diagram showing a pulse sequence of this prior art example. Waveforms shown in FIG. 24 represent, from top to bottom, an electrocardiograph (ECG) as a synchronization waveform, a radio-frequency (RF) pulse applied to an imaging target, a slice direction gradient magnetic field waveform (Gss), a readout direction gradient magnetic field waveform (Gro), a phase encoding direction gradient magnetic field waveform (Gpe), and a deviation ($\Delta f$) of a carrier wave from a center frequency during the application of the radio-frequency pulse. A period P1 is a tag (label) sequence part for labeling the blood or cerebrospinal fluid, and a period P2 is a main pulse sequence part for imaging. For periods P1 and P2, a combination of gradient magnetic field strengths and $\Delta f$ can be independently set at the time of the selective excitation, and the direction and position of an excited surface can be independently set. Although a case of a fast spin echo method is shown in this example, it is possible to use any imaging method such as a coherent gradient echo method (a true SSFP method, true FISP or balanced FFE method). The number of shots necessary to reconstruct one image is collected during the same inversion time TI. The imaging is repeated with variations in this inversion time TI. A plurality of images taken at different inversion times TI are sequentially displayed to enable the observation of the dynamic state of the cerebrospinal fluid. With regard to parts with motion among parts excited by a labeling pulse LP in period P1, portions outside a labeling region show a low signal intensity on the image because of motion corresponding to a flow velocity during the inversion time TI. This permits the observation of the motion of the blood or cerebrospinal fluid. Another example has been shown wherein one more nonselective IR pulse is added before or after an RF pulse in period P1 in terms of time such that the longitudinal magnetization of the labeled part is substantially brought to an initial state, thereby imaging the motion of the blood or cerebrospinal fluid as a high signal intensity.

As measurement means for the motion of the cerebrospinal fluid, there are also known, for example, a method wherein a radioisotope is injected into a spinal cavity and its motion in a body is traced by several hours by means such as a scintillation counter, and a method that uses a contrast media (metrizamide) to perform a measurement in the same manner by X-ray computed tomography (CT). In spite of an advantage of facilitating the observation of the long-time motion called bulk motion of the cerebrospinal fluid, all of these methods entail a high degree of invasiveness of a test subject. Moreover, since the radioisotope or contrast media is injected in these methods, the inner pressure of the cerebrospinal fluid might change, which affects an observation target.

First Problem: if the inversion time TI is changed, a time from a reference time point to imaging (times TDseq1, TDseq2 in FIG. 24) changes as much as the change of the inversion time TI in the case where the method shown in Japanese Patent Application KOKAI Publication No. 2001-252263 is used to observe the dynamic state of the blood or cerebrospinal fluid. Thus, the flow velocity of the blood or cerebrospinal fluid during collection varies every imaging, so that there is a disadvantage that a signal value changes due to effects other than the difference of the inversion time TI or the capability to visualize the blood or cerebrospinal fluid varies every imaging. Especially when, for example, a fast spin echo method is employed that uses a Carr-Purcell-Meiboom-Gill (CPMG) pulse sequence as a main pulse sequence, an image is formed as the composition of a plurality of echo components with different phase variations due to flow Velocities, and this leads to sharp changes in image values corresponding to the flow velocities due to the interferential action of phases, which is a serious problem.

Second Problem: in the case where the imaging target is the cerebrospinal fluid, the correlation with the cardiac phase is not necessarily high, and the pulsation regularity of the cerebrospinal fluid tends to be lower than that of blood. Therefore, in the case of the observation target such as the cerebrospinal fluid, there has been a disadvantage that it is not easy to judge whether a change is caused by individual imaging variations or by the variation of the inversion time TI, even if images with the sequentially changed inversion time TI are compared.

Third Problem: in normal labeling methods, there has been a disadvantage that it is not easy to know the motion of the cerebrospinal fluid or blood in the whole two- or three-dimensional region because the labeling region is limited to a straight form.

Fourth Problem: when an imaging section is set out of a normal positioning image, it is not easy to set a labeling region at a proper position because a portion with a suspected lesion of the blood or cerebrospinal fluid is unclear on the positioning image for labeling, and there has been a disadvantage that it is not easy to visualize the motion of the cerebrospinal fluid or blood.

Fifth Problem: there has been a disadvantage that clinical knowledge of the circulatory pathways of the cerebrospinal fluid or blood is required for a user of an apparatus in order to carry out the imaging using labeling, and properly setting imaging conditions is difficult.

BRIEF SUMMARY OF THE INVENTION

Under such circumstances, it has been firstly desired to be able to obtain an image that accurately indicates a change of a signal value with the difference of an inversion time TI and that visualizes a moving material with a stable visualization capability.

It has been secondly desired to be able to obtain a plurality of images that visualize the moving material with timings synchronized with its pulsation to a high degree.

It has been thirdly desired to be able to obtain an image useful to know the motion of the moving material from more sides.

It has been fourthly desired to be able to easily set a labeling region.

It has been fifthly desired to be able to easily and properly set imaging conditions.

According to a first aspect of the present invention, there is provided a magnetic resonance imaging apparatus that generates a magnetic resonance image on the basis of an echo signal regarding a spin included in an imaging region of a subject, the apparatus comprising: an imaging unit that applies a labeling pulse to invert the spin included in a labeling region within part of the imaging region and then collects the echo signal from a time point when an inversion time has passed from the application of the labeling pulse; and a control unit, the control unit controlling the imaging unit so that the echo signal in the imaging region is collected a plurality of times with variations in the inversion time, the control unit also controlling the imaging unit so that a time ranging from a reference time point within a biological signal obtained from the subject to the application of the labeling pulse is a time determined in accordance with the inversion time.

According to a second aspect of the present invention, there is provided a magnetic resonance imaging apparatus that generates a magnetic resonance image on the basis of an echo signal regarding a spin included in an imaging region of a subject, the apparatus comprising: an imaging unit that applies a labeling pulse to invert the spin included in a labeling region within part of the imaging region and then applies an excitation pulse at a time point when an inversion time has passed from the application of the labeling pulse in order to collect the resulting echo signal; and a control unit, the control unit controlling the imaging unit so that the echo signal in the imaging region is collected a plurality of times with variations in the inversion time, the control unit also controlling the imaging unit so that a time ranging from a reference time point within a biological signal obtained from the subject to the application of the excitation pulse is constant regardless of the inversion time in the plurality of collections of the echo signal.

According to a third aspect of the present invention, there is provided a magnetic resonance imaging apparatus comprising: an acquisition unit that acquires an echo signal regarding a spin included in an imaging region of a subject in accordance with a predetermined pulse sequence; a reconstruction unit that reconstructs an image of the inside of the imaging region in accordance with the acquired echo signal; a labeling unit that inverts the spin included in a labeling region within part of the imaging region to conduct labeling; and a control unit, the control unit controlling the labeling unit and the acquisition unit so that a cycle of conducting the labeling and acquiring the echo signal from a time point when a first time has passed from a time point of the labeling is carried out a plurality of times with variations in the first time, the control unit also controlling the labeling unit and the acquisition unit so that each of the plurality of cycles is started at a time point when a second time that increases or decreases contrary to the size of the first time in each cycle has passed from a periodic reference time point.

According to a fourth aspect of the present invention, there is provided a magnetic resonance imaging apparatus comprising: an acquisition unit that acquires an echo signal regarding a spin included in an imaging region of a subject in accordance with a predetermined pulse sequence; a reconstruction unit that reconstructs an image of the inside of the imaging region in accordance with the acquired echo signal; a labeling unit that inverts the spin included in a labeling region within part of the imaging region to conduct labeling; and a control unit, the control unit controlling the labeling unit and the acquisition unit so that a cycle of conducting the labeling and acquiring the echo signal from a time point when a given first time has passed from a time point of the labeling is carried out a plurality of times without changing the labeling region, the control unit also controlling the labeling unit and the acquisition unit so that each of the plurality of cycles is started at a time point when a given second time has passed from a periodic reference time point.

According to a fifth aspect of the present invention, there is provided a magnetic resonance imaging apparatus comprising: an acquisition unit that acquires an echo signal regarding a spin included in an imaging region of a subject in accordance with a predetermined pulse sequence; a reconstruction unit that reconstructs an image of the inside of the imaging region in accordance with the acquired echo signal; a labeling unit that inverts the spin included in a labeling region within part of the imaging region to conduct labeling; an observation unit that repetitively acquires a magnetic resonance signal from within the labeling region and observes a change of the flow velocity of a fluid in the labeling region on the basis of a change of the repetitively acquired magnetic resonance signal; and a control unit, the control unit controlling the labeling unit and the acquisition unit so that a cycle of conducting the labeling and acquiring the echo signal from a time point when a predetermined first time has passed after the labeling is carried out a plurality of times, the control unit also controlling the labeling unit and the acquisition unit so that the cycle is started at a time point when a predetermined second time has passed from a reference time point at which the observed change of the flow velocity coincides with a predetermined state.

According to a sixth aspect of the present invention, there is provided a magnetic resonance imaging apparatus comprising: an acquisition unit that acquires an echo signal regarding a spin included in an imaging region of a subject in accordance with a predetermined pulse sequence; a reconstruction unit that reconstructs an image of the inside of the imaging region in accordance with the acquired echo signal;

a labeling unit that inverts the spin included in the imaging region and then inverts the spin included in each of a plurality of labeling regions within part of the imaging region to conduct labeling; and a control unit, the control unit controlling the labeling unit and the acquisition unit so that a cycle of conducting the labeling and acquiring the echo signal from a time point when a predetermined first time has passed from a time point of the labeling is carried out a plurality of times, the control unit also controlling the labeling unit and the acquisition unit so that the cycle is started at a time point when a predetermined second time has passed from a periodic reference time point.

According to a seventh aspect of the present invention, there is provided a magnetic resonance imaging apparatus comprising: an acquisition unit that acquires an echo signal regarding a spin included in an imaging region of a subject in accordance with a predetermined pulse sequence; a reconstruction unit that reconstructs an image of the inside of the imaging region in accordance with the acquired echo signal; a labeling unit that inverts the spin included in a labeling region within part of the imaging region to conduct labeling; a control unit, the control unit controlling the labeling unit and the acquisition unit so that a cycle of conducting the labeling and acquiring the echo signal from a time point when a predetermined first time has passed after the labeling is carried out a plurality of times, the control unit also controlling the labeling unit and the acquisition unit so that each of the plurality of cycles is started at a time point when a predetermined second time has passed from a periodic reference time point; a unit that displays, as a positioning image, one of the plurality of images reconstructed on the basis of the echo signal acquired in each of the plurality of cycles; and a unit that accepts a designation of an imaging section on the positioning image.

According to an eighth aspect of the present invention, there is provided a magnetic resonance imaging apparatus having access to a storage device, the apparatus comprising: an acquisition unit that acquires an echo signal regarding a spin included in an imaging region of a subject in accordance with a predetermined pulse sequence; a reconstruction unit that reconstructs an image of the inside of the imaging region in accordance with the acquired echo signal; a labeling unit that inverts the spin included in a labeling region within part of the imaging region to conduct labeling; a control unit, the control unit controlling the labeling unit and the acquisition unit so that a cycle of conducting the labeling and acquiring the echo signal from a time point when a predetermined first time has passed after the labeling is carried out a plurality of times, the control unit also controlling the labeling unit and the acquisition unit so that each of the plurality of cycles is started at a time point when a predetermined second time has passed from a periodic reference time point; and a unit that sets the labeling region on the basis of information stored in the storage device.

According to a ninth aspect of the present invention, there is provided a magnetic resonance imaging method that generates a magnetic resonance image on the basis of an echo signal regarding a spin included in an imaging region of a subject, the method comprising: applying a labeling pulse to invert the spin included in a labeling region within part of the imaging region and then collecting the echo signal from a time point when an inversion time has passed from the application of the labeling pulse; and collecting the echo signal in the imaging region a plurality of times with variations in the inversion time, and also controlling the application of the labeling pulse and the collection so that a time ranging from a reference time point within a biological signal obtained from the subject to the application of the labeling pulse is a time determined in accordance with the inversion time.

According to a tenth aspect of the present invention, there is provided a magnetic resonance imaging method that generates a magnetic resonance image on the basis of an echo signal regarding a spin included in an imaging region of a subject, the method comprising: applying a labeling pulse to invert the spin included in a labeling region within part of the imaging region and then applying an excitation pulse at a time point when an inversion time has passed from the application of the labeling pulse in order to collect the resulting echo signal; and controlling the application of the labeling pulse and the collection so that the echo signal in the imaging region is collected a plurality of times with variations in the inversion time, and also controlling the application of the labeling pulse and the collection so that a time ranging from a reference time point within a biological signal obtained from the subject to the application of the excitation pulse is constant regardless of the inversion time in the plurality of collections of the echo signal.

According to a eleventh aspect of the present invention, there is provided a magnetic resonance imaging method comprising: acquiring an echo signal regarding a spin included in an imaging region of a subject in accordance with a predetermined pulse sequence; reversing the spin included in a labeling region within part of the imaging region to conduct labeling; controlling the labeling and the acquisition so that a cycle of conducting the labeling and acquiring the echo signal from a time point when a first time has passed from a time point of the labeling is carried out a plurality of times with variations in the first time, and also controlling the labeling and the acquisition so that each of the plurality of cycles is started at a time point when a second time that increases or decreases contrary to the size of the first time in each cycle has passed from a periodic reference time point; and reconstructing an image of the inside of the imaging region in accordance with the acquired echo signal.

According to a twelfth aspect of the present invention, there is provided a magnetic resonance imaging method comprising: acquiring an echo signal regarding a spin included in an imaging region of a subject in accordance with a predetermined pulse sequence; reversing the spin included in a labeling region within part of the imaging region to conduct labeling; controlling the labeling and the acquisition so that a cycle of conducting the labeling and acquiring the echo signal from a time point when a given first time has passed from a time point of the labeling is carried out a plurality of times without changing the labeling region, and also controlling the labeling and the acquisition so that each of the plurality of cycles is started at a time point when a given second time has passed from a periodic reference time point; and reconstructing an image of the inside of the imaging region in accordance with the acquired echo signal.

According to a thirteenth aspect of the present invention, there is provided a magnetic resonance imaging method comprising: acquiring an echo signal regarding a spin included in an imaging region of a subject in accordance with a predetermined pulse sequence; reversing the spin included in a labeling region within part of the imaging region to conduct labeling; repetitively acquiring a magnetic resonance signal from within the labeling region and observing a change of the flow velocity of a fluid in the labeling region on the basis of a change of the repetitively acquired magnetic resonance signal; controlling the labeling and the acquisition so that a cycle of conducting the labeling and acquiring the echo signal from a time point when a predetermined first time has passed after the labeling is carried out a plurality of times, and also controlling the labeling and the acquisition so that the cycle is started at a time point when a predetermined second time has passed from a reference time point at which the observed change of the flow velocity coincides with a predetermined state; and reconstructing an image of the inside of the imaging region in accordance with the acquired echo signal.

According to a fourteenth aspect of the present invention, there is provided a magnetic resonance imaging method comprising: acquiring an echo signal regarding a spin included in an imaging region of a subject in accordance with a predetermined pulse sequence; reversing the spin included in the imaging region and then reversing the spin included in each of a plurality of labeling regions within part of the imaging region to conduct labeling; and controlling the labeling and the acquisition so that a cycle of conducting the labeling and acquiring the echo signal from a time point when a predetermined first time has passed from a time point of the labeling is carried out a plurality of times, and also controlling the labeling and the acquisition so that the cycle is started at a time point when a predetermined second time has passed from a periodic reference time point; reconstructing an image of the inside of the imaging region in accordance with the acquired echo signal.

According to a fifteenth aspect of the present invention, there is provided a magnetic resonance imaging method comprising: acquiring an echo signal regarding a spin included in an imaging region of a subject in accordance with a predetermined pulse sequence; reversing the spin included in a labeling region within part of the imaging region to conduct labeling; controlling the labeling and the acquisition so that a cycle of conducting the labeling and acquiring the echo signal from a time point when a predetermined first time has passed after the labeling is carried out a plurality of times, and also controlling the labeling and the acquisition so that each of the plurality of cycles is started at a time point when a predetermined second time has passed from a periodic reference time point; reconstructing an image of the inside of the imaging region in accordance with the acquired echo signal; displaying, as a positioning image, one of the plurality of images reconstructed on the basis of the echo signal acquired in each of the plurality of cycles; and accepting a designation of an imaging section on the positioning image.

According to a sixteenth aspect of the present invention, there is provided a magnetic resonance imaging method in a magnetic resonance imaging apparatus having access to a storage device, the method comprising: acquiring an echo signal regarding a spin included in an imaging region of a subject in accordance with a predetermined pulse sequence; reversing the spin included in a labeling region within part of the imaging region to conduct labeling; controlling the labeling and the acquisition so that a cycle of conducting the labeling and acquiring the echo signal from a time point when a predetermined first time has passed from a time point of the labeling is carried out a plurality of times, and also controlling the labeling and the acquisition so that each of the plurality of cycles is started at a time point when a predetermined second time has passed from a periodic reference time point; setting the labeling region on the basis of information stored in the storage device; and reconstructing an image of the inside of the imaging region in accordance with the acquired echo signal.

Additional objects and advantages of the invention will be set forth in the description that follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 10 is a diagram showing another example of how the excitation region and the observation region are set in the second embodiment;

FIG. 15 is a diagram showing an example of how a labeling region is set in the fourth embodiment;

FIG. 16 is a diagram explaining one example of a section suitable to obtaining a positioning image for setting the labeling region in the fourth embodiment;

FIG. 17 is a diagram showing a two-dimensional image taken in a section S1 shown in FIG. 16 and an example of how to set labeling regions in this image;

FIG. 18 is a diagram showing one example of an image taken by the pulse sequence in the fourth embodiment when labeling regions R11 and R12 are set as shown in FIG. 17;

FIG. 19 is a diagram showing one example of a positioning image in a fifth embodiment;

FIG. 20 is a diagram showing an example of how to set an imaging section on the positioning image shown in FIG. 19;

FIG. 21 is a diagram showing a two-dimensional image taken in a section S11 shown in FIG. 20;

FIG. 22 is a diagram showing one example of an image obtained by imaging after labeling a labeling region R23 as shown in FIG. 21;

DETAILED DESCRIPTION OF THE INVENTION

Hereinafter, first to seventh embodiments of the present invention will be described with reference to the drawings.

Figure 1:
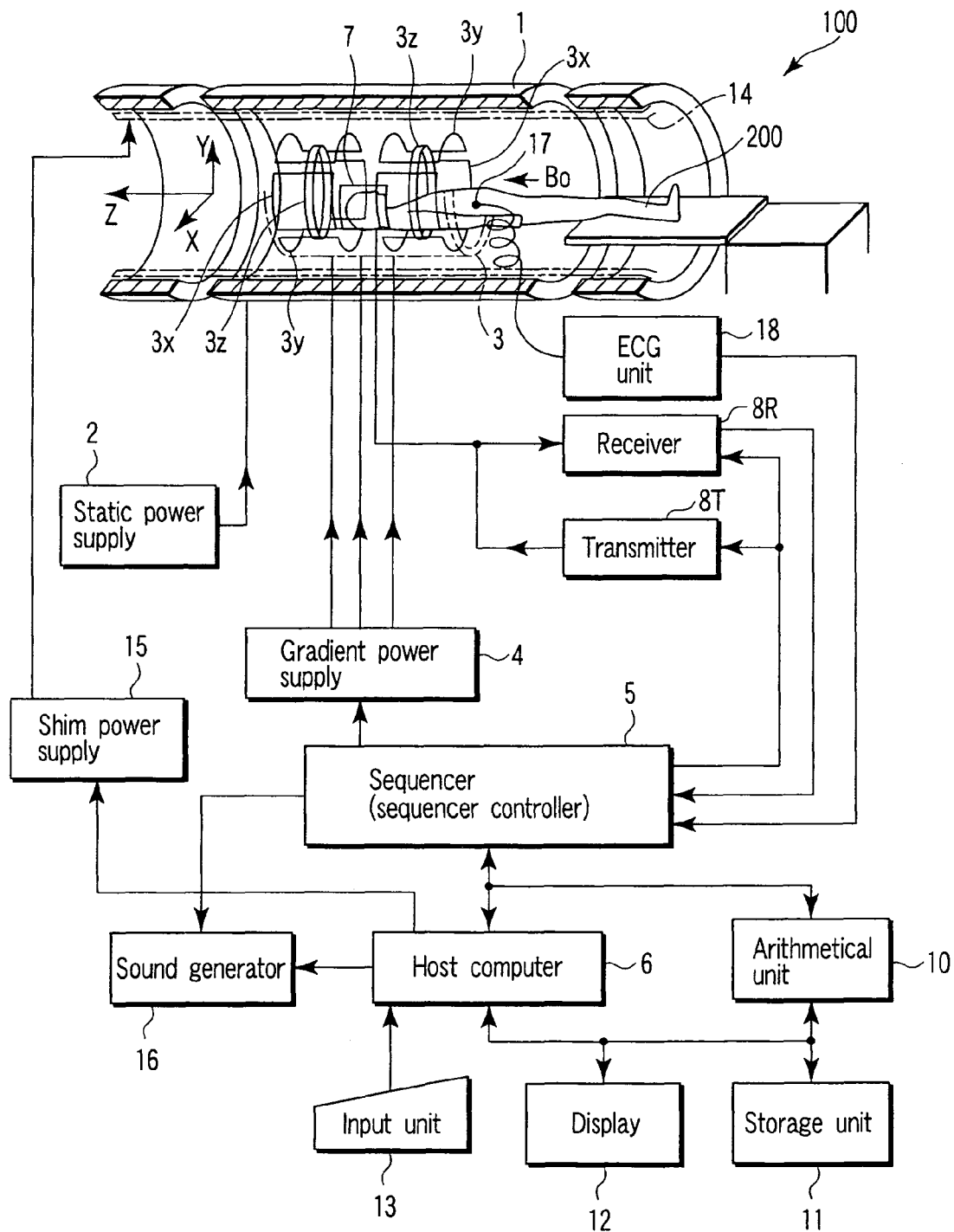
FIG. 1 is a diagram showing the configuration of a magnetic resonance imaging apparatus according to first to seventh embodiments of the present invention.

FIG. 1 is a diagram showing the configuration of a magnetic resonance imaging apparatus (hereinafter referred to as an MRI apparatus) 100 according to the first to seventh embodiments.

The MRI apparatus 100 comprises a bed on which a subject 200 is mounted, a static magnetic field generator for generating a static magnetic field, a gradient magnetic field generator for adding positional information to the static magnetic field, a transmitter/receiver for transmitting/receiving a high-frequency signal, and a controller/computer responsible for the control of the whole system and image reconstruction. As components of these parts, the MRI apparatus 100 has a magnet 1, a static power supply 2, a gradient coil unit 3, a gradient power supply 4, a sequencer (sequence controller) 5, a host computer 6, an RF coil unit 7, a transmitter 8T, a receiver 8R, an arithmetical unit 10, a storage unit 11, a display 12, an input unit 13, a shim coil 14 and a shim power supply 15. The MRI apparatus 100 further comprises an electrocardiographic measure for measuring an ECG signal as a signal indicating a cardiac phase of the subject 200, a breath-holding instructor for instructing the subject 200 to hold breath. Components of the electrocardiographic measure and the breath-holding instructor include a sound generator 16, an ECG sensor 17 and an ECG unit 18.

The static magnetic field generator includes the magnet 1 and the static power supply 2. For example, a superconducting magnet or a normal conducting magnet can be used as the magnet 1. The static power supply 2 supplies a current to the magnet 1. Thus, the static magnetic field generator generates a static magnetic field $B_0$ in a cylindrical space (diagnostic space) into which the subject 200 is sent. The direction of this static magnetic field $B_0$ substantially coincides with the axial direction (Z axis direction) of the diagnostic space. The static magnetic field generator is further provided with the shim coil 14. This shim coil 14 is supplied with a current from the shim power supply 15 under the control of the host computer 6 and generates a correcting magnetic field for homogenizing the static magnetic field.

The bed sends a top board on which the subject 200 is mounted into the diagnostic space or pulls it out of the diagnostic space.

The gradient magnetic field generator includes the gradient coil unit 3 and the gradient power supply 4. The gradient coil unit 3 is disposed inside the magnet 1. The gradient coil unit 3 comprises three sets of coils $3x$, $3y$ and $3z$ for generating gradient magnetic fields in the X axis direction, Y axis direction and Z axis direction that are perpendicular to each other. The gradient power supply 4 supplies pulse currents for generating the gradient magnetic fields in the coils $3x$, $3y$ and $3z$ under the control of the sequencer 5. Thus, the gradient magnetic field generator controls the pulse currents supplied from the gradient power supply 4 to the coils $3x$, $3y$ and $3z$ to synthesize the gradient magnetic fields in the directions of the three axes (X axis, Y axis and Z axis) that are physical axes, thereby arbitrarily setting gradient magnetic fields in logical axis directions including slice direction gradient magnetic field Gss, a phase encoding direction gradient magnetic field Gpe and readout direction (frequency encoding direction) gradient magnetic field Gro that are perpendicular to each other. The gradient magnetic fields Gss, Gpe and Gro in the slice direction, phase encoding direction and readout direction are superposed on the static magnetic field $B_0$.

The transmitter/receiver includes the RF coil unit 7, the transmitter 8T and the receiver 8R. The RF coil unit 7 is disposed in the vicinity of the subject 200 in the diagnostic space. The transmitter 8T and the receiver 8R are connected to the RF coil unit 7. The transmitter 8T and the receiver 8R operate under the control of the sequencer 5. The transmitter 8T supplies RF current pulses at Larmor frequency for causing nuclear magnetic resonance (NMR) to the RF coil unit 7. The receiver 8R imports an MR signal (high-frequency signal) such as an echo signal received by the RF coil unit 7, and subjects it to various signal processing such as preamplification, intermediate frequency conversion, phase detection, low-frequency amplification and filtering, and then subjects the signal to A/D conversion to generate echo data (raw data) in a digital quantity corresponding to the echo signal.

The controller/computer includes the sequencer 5, the host computer 6, the arithmetical unit 10, the storage unit 11, the display 12 and the input unit 13.

The sequencer 5 comprises a CPU and a memory. The sequencer 5 stores pulse sequence information sent from the host computer 6 in the memory. The CPU of the sequencer 5 controls the operations of the gradient power supply 4, the transmitter 8T and the receiver 8R in accordance with the sequence information stored in the memory, and also temporarily inputs the echo data output by the receiver 8R and transfers it to the arithmetical unit 10. Here, the sequence information is the whole information necessary to operate the gradient power supply 4, the transmitter 8T and the receiver 8R in accordance with a series of pulse sequences, and includes information regarding, for example, the intensity of the pulse currents applied to the coils $3x$, $3y$ and $3z$, application time, and application timing.

The host computer 6 has various functions achieved by carrying out a predetermined software procedure. One of the functions is to instruct the sequencer 5 on the sequence information and perform the overall control of the operation of the whole apparatus. One of the functions is to control the sequencer 5 to collect the echo signals in an imaging region a plurality of times with a varying inversion time, and to control the sequencer 5 so that a time from a reference time point in the ECG signal to the application of labeling pulses may be a proper time. Further, functions provided in the host computer can include the following functions. One of the functions is to repetitively acquire a magnetic resonance signal from within a labeling region, and observe the change of the flow velocity of a fluid in the labeling region on the basis of the change of the repetitively acquired magnetic resonance signal. One of the functions is to display one of a plurality of images reconstructed on the basis of the echo signals acquired by the plurality of collections, as a positioning image on the display 12. One of the functions is to accept the designation of an imaging section on the positioning image. One of the functions is to set the labeling region on the basis of the information stored in the storage unit 11.

The host computer 6 performs an imaging scan after preparatory tasks such as a positioning scan. The imaging scan is a scan for collecting a set of echo data necessary for the image reconstruction, and is set here to a two-dimensional scan. The imaging scan can be performed in combination with an ECG gate method based on the ECG signal. In addition, this ECG gate method does not have to be used in combination in some cases.

The pulse sequence includes a three-dimensional (3D) or two-dimensional (2D) scan. For the form of its pulse train, use is made of, for example, a spin echo (SE) method, a fast spin echo (FSE) method, a fast asymmetric spin echo (FASE) method that is a combination of the fast SE method and a half-Fourier method, or an echo planar imaging (EPI) method.

The echo data output by the receiver 8R is input to the arithmetical unit 10 through the sequencer 5. The arithmetical unit 10 disposes the input echo data in a Fourier space (also referred to as a k space or a frequency space) set in an internal memory. The arithmetical unit 10 subjects the echo data disposed in the Fourier space to two- or three-dimensional Fourier transformation to reconstruct real-space image data. The arithmetical unit 10 can also perform synthesizing processing and difference computing processing for data on the image as necessary.

The synthesizing processing includes, for example, addition processing for adding image data for a plurality of two-dimensional frames with respect to each corresponding pixel, and maximum intensity projection (MIP) processing or minimum intensity projection processing for selecting a maximum value or minimum value in a sight line direction for three-dimensional data. Another example of the synthesizing processing may be to align the axes of a plurality of frames on the Fourier space to synthesize them with the echo data for one frame without changing the echo data. In addition, the addition processing includes simple addition processing, averaging processing, weighting addition processing, etc.

The storage unit 11 stores the reconstructed image data and the image data subjected to the above-mentioned synthesizing processing and difference processing.

The display 12 indicates various images to be presented to a user under the control of the host computer 6. A display device such as a liquid crystal display can be used as the display 12.

Input to the input unit 13 are various kinds of information such as imaging conditions desired by an operator, the pulse sequence, and information regarding the synthesizing processing and difference computing. The input unit 13 sends the input information to the host computer 6. The input unit 13 to be suitably provided is, for example, a pointing device such as a mouse or a track ball, a selecting device such as a mode change switch, or an input device such as a keyboard.

The breath-holding instructor comprises the sound generator 16. The sound generator 16 generates messages for the start and end of breath holding as sounds under the control of the host computer 6.

The electrocardiographic measure includes the ECG sensor 17 and the ECG unit 18. The ECG sensor 17 is attached to the surface of the body of the subject 200, and detects the ECG signal of the subject 200 as an electric signal (hereinafter referred to as a sensor signal). The ECG unit 18 subjects the sensor signal to various processing including digitization, and then outputs it to the sequencer 5 and the host computer 6. The sensor signal is used by the sequencer 5 when the imaging scan is performed. This makes it possible to properly set synchronization timing by the ECG gate method (electro-cardio-graphic synchronization method), and the imaging scan of the ECG gate method based on this synchronization timing can be performed to collect data.

The operation of the MRI apparatus 100 configured as described above will next be described in detail.

First Embodiment

The first embodiment is described below. The first embodiment corresponds to First Problem.

Figure 2:
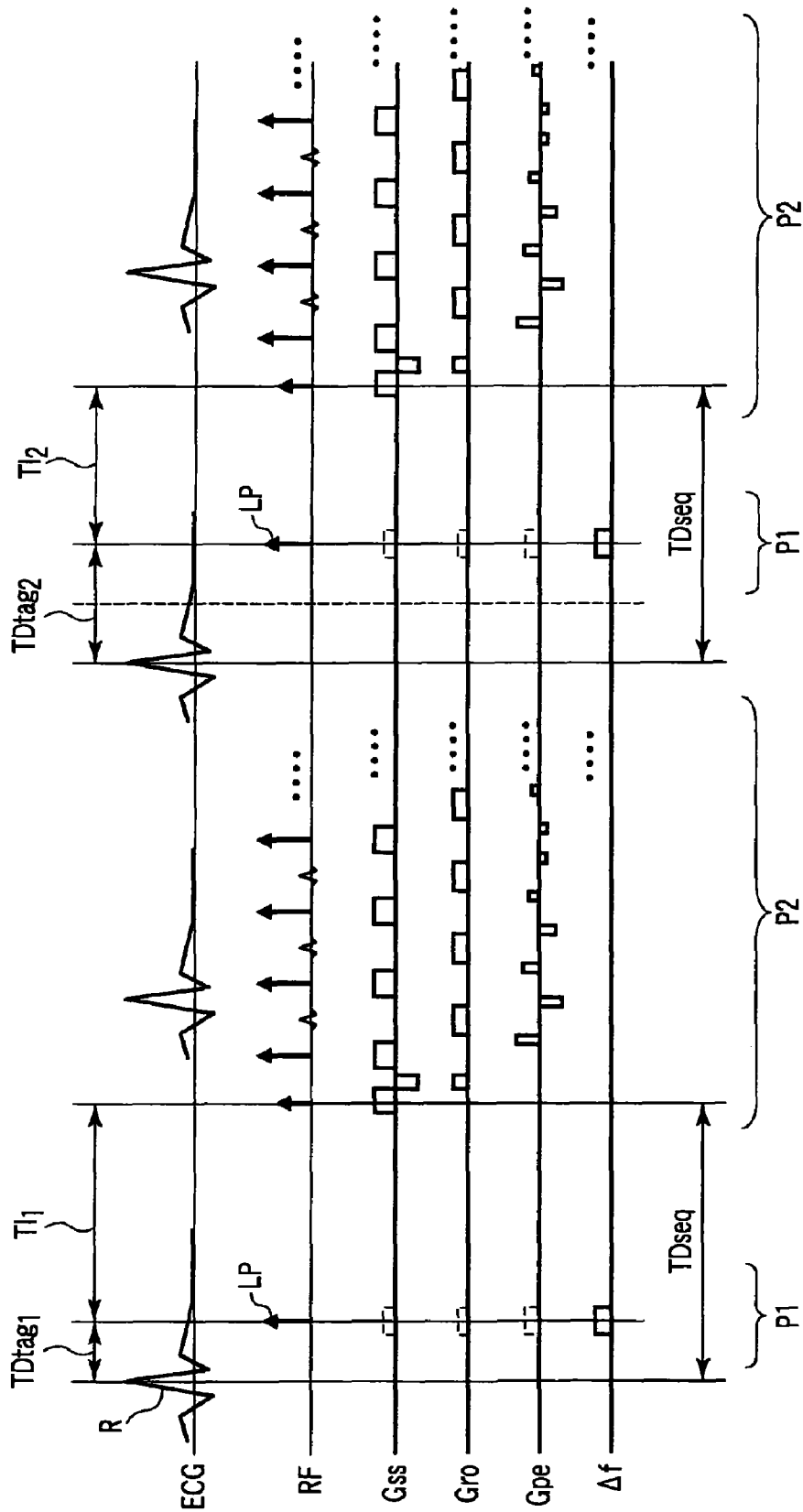
FIG. 2 is a diagram showing a pulse sequence in a first embodiment.

FIG. 2 is a diagram showing a pulse sequence in the first embodiment. Waveforms shown in FIG. 2 represent, from top to bottom, an ECG as a synchronization waveform, a radio-frequency (RF) pulse applied to an imaging target, a slice direction gradient magnetic field waveform (Gss), a readout direction gradient magnetic field waveform (Gro), a phase encoding direction gradient magnetic field waveform (Gpe), and a deviation (Δf) of a carrier wave from a center frequency during the application of the radio-frequency pulse. A period P1 is a tag sequence part for labeling blood or cerebrospinal fluid. A period P2 is a main pulse sequence part for imaging. Although a fast spin echo method is employed in this example, it is possible to use any imaging method such as the coherent gradient echo method (the true SSFP method, true FISP or balanced FFE method).

Figure 24:
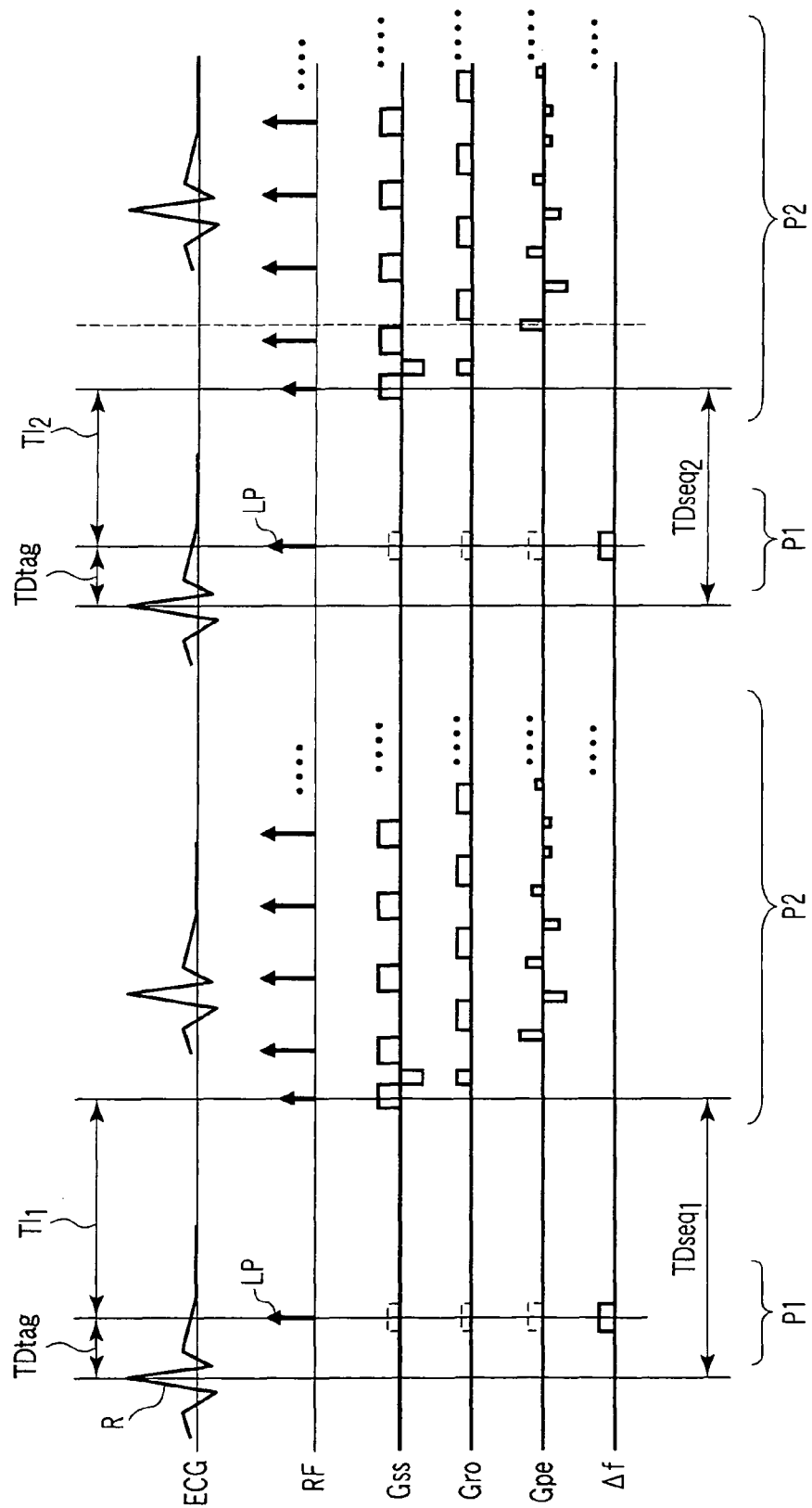
FIG. 24 is a diagram showing a pulse sequence disclosed in Japanese Patent Application KOKAI Publication No. 2001-252263.

As apparent from a comparison between FIGS. 2 and 24, the pulse sequence in the first embodiment is based on the pulse sequence disclosed in Japanese Patent Application KOKAI Publication No. 2001-252263. That is, an imaging cycle comprising labeling in period P1 and echo collection in period P2 is repeated a plurality of times with variations in the size of an inversion time TI ranging from excitation by a labeling pulse LP to the start of the pulse sequence for the echo collection. The pulse sequence in the first embodiment is different from the pulse sequence in FIG. 24 in which a time TDtag ranging from a reference time point to the excitation by the labeling pulse LP is changed contrary to the size of the inversion time TI in every imaging cycle. In addition, a time point in which an R wave is appeared in the ECG is the reference time point.

Figure 3:
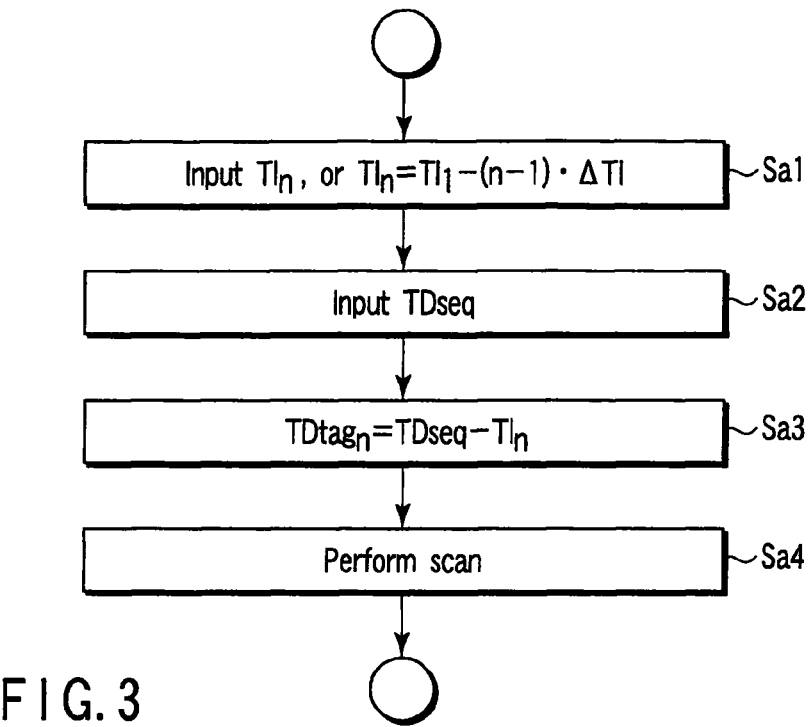
FIG. 3 is a flowchart for the processing of a host computer in FIG. 1 for condition setting.

FIG. 3 is a flowchart for the processing of the host computer 6 for condition setting.

In step Sa1, input to the host computer 6 is the value of an inversion time $TI_n$ designated by, for example, an operator for each of the plurality of imaging cycles, or are the number of imaging cycles, the value of an inversion time $TI_1$ in the first imaging cycle and a variation $\Delta TI$ of the inversion time TI, designated by, for example, the operator thereby calculating the inversion time $TI_n$ for an n-th imaging cycle in accordance with a predetermined equation. For example, the following equation can be applied as such an equation.

$$TI_n = TI_1 - (n-1) \cdot \Delta TI$$

In step Sa2, input to the host computer 6 is a value designated by, for example, the operator as a time TDseq ranging from the reference time point to the start of the pulse sequence for echo collection.

The various values input in step Sa1 and step Sa2 may be in any form, such as a default value or a value selected by the operator from a plurality of default values. Moreover, the various values may be input in any order.

In step Sa3, the host computer 6 calculates a time $TDtag_n$ for each of the plurality of imaging cycles.

$$TDtag_n = TDseq - TI_n$$

In addition, since $TDtag_n$ generally has to be zero or a positive value for convenience of the control of the apparatus, the control may be limited as necessary so that TDseq is equal to or more than the maximum value of $TI_n$ when TDseq is input.

In step Sa4, the host computer 6 performs a scan in accordance with the pulse sequence shown in FIG. 2. At this time, the host computer 6 instructs the sequencer 5 to apply the time $TDtag_n$ and the inversion time $TI_n$ in the n-th imaging cycle. In accordance with this instruction, the sequencer 5 repetitively performs the imaging cycles with variations in the time TDtag and the inversion time TI. In the example in FIG. 2, while an inversion time $TI_2$ in the second imaging cycle is smaller than the inversion time $TI_1$ in the first imaging cycle, a time TDtag2 in the second imaging cycle is, on the contrary, larger than a time TDtag1 in the first imaging cycle.

A plurality of images reconstructed on the basis of the echo data collected in every imaging cycle are sequentially displayed such that information useful to observe the dynamic state of the blood or cerebrospinal fluid can be presented. That is, portions that are not labeled on the image show a low signal intensity because the motion is made in accordance with a flow velocity during the inversion time TI in a part with motion among parts excited by the labeling pulse LP in period P1. If this part is traced on each image, the motion of the blood or cerebrospinal fluid can be observed.

On the other hand, in the first embodiment, the time TDtag is in inverse proportion to the inversion time TI, so that the time TDseq is the same in each of the imaging cycles. Thus, while the inversion time TI is changed to visualize the dynamic state of the blood or cerebrospinal fluid, the time TDseq ranging from the reference time point to the start of the pulse sequence for echo collection is uniform in the imaging cycles. Therefore, each of the imaging cycles accurately synchronizes with the ECG, such that the influence of periodic changes with pulsation is held down and a change and image artifacts in each imaging can be suppressed.

When, for example, the fast spin echo method is employed that uses the CPMG pulse sequence as the main pulse sequence, an image is formed as the composition of a plurality of echo components with different phase variations due to flow velocities, and this leads to a sharp changes in image values corresponding to the flow velocities due to the interferential action of phases. Thus, the reduction of the image variation owing to the homogeneity of the time TDseq in the imaging cycles in accordance with the first embodiment is more evident than in other pulse sequences and is particularly effective.

In addition, it is also possible to employ a pulse sequence requiring a plurality of shots to reconstruct one image. In this case, a procedure may be taken that repeats echo collections corresponding to the number of shots necessary for reconstructing one image without changing the inversion time TI and further repeats this processing with variations in the inversion time TI.

Figure 4:
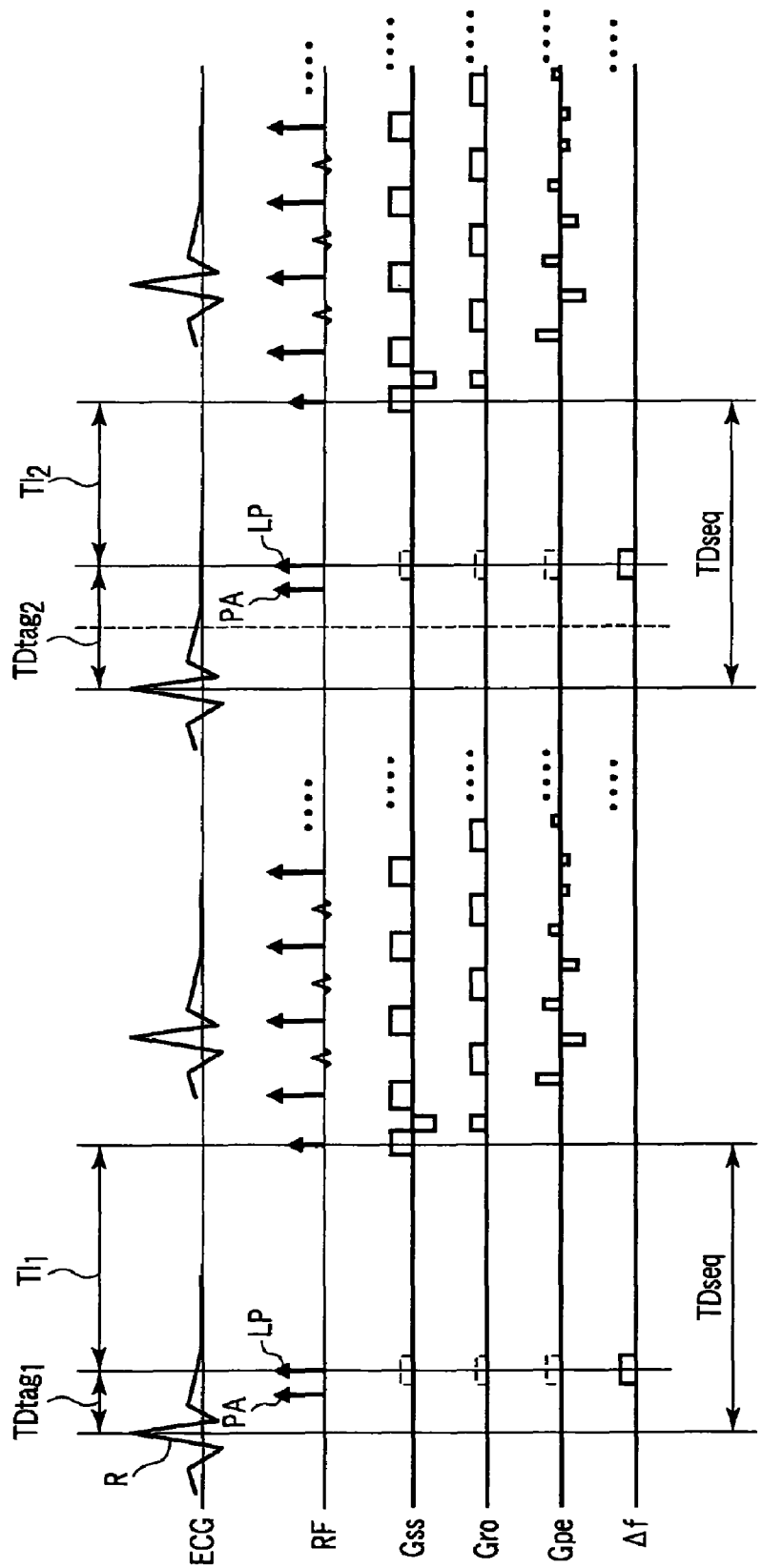
FIG. 4 is a diagram showing a modification of the pulse sequence in the first embodiment.

Furthermore, as shown in FIG. 4, an IR pulse (180 degree pulse) PA may be added before the labeling pulse LP in a slice non-selection state (where a slice gradient magnetic field is zero during RF application). This brings the longitudinal magnetization of the labeled part to nearly an initial state, so that the motion of the blood or cerebrospinal fluid can be imaged as a high signal intensity. That is, it is possible to obtain a negative/positive inversion of the image obtained by the pulse sequence shown in FIG. 2.

Second Embodiment

The second embodiment is described below. The second embodiment corresponds to Second Problem.

Figure 5:
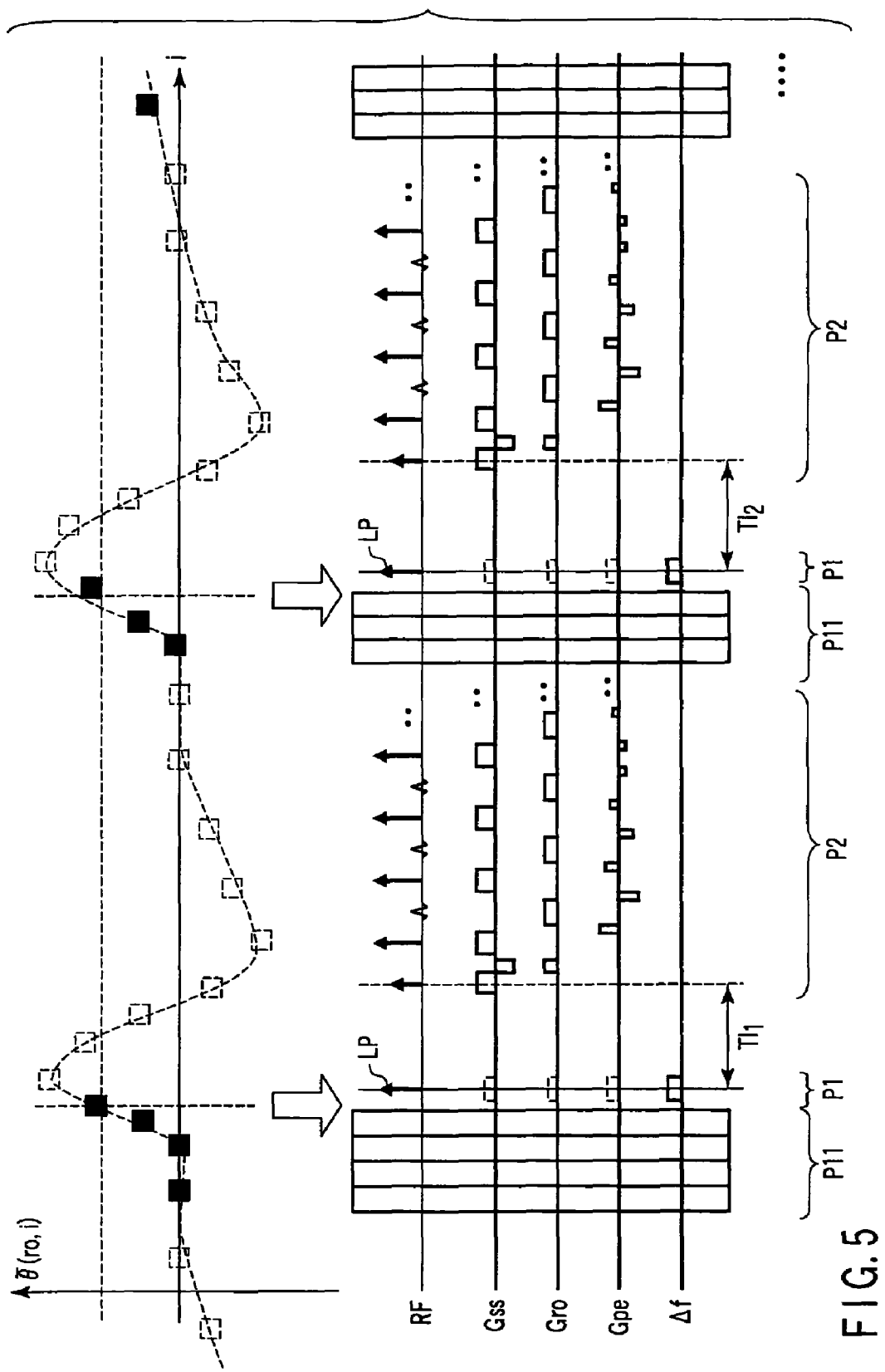
FIG. 5 is a diagram showing a pulse sequence in a second embodiment.

FIG. 5 is a diagram showing a pulse sequence in the second embodiment. Waveforms shown in FIG. 5 represent, from top to bottom, a cerebrospinal fluid pulsation waveform as a synchronization waveform, a radio-frequency (RF) pulse applied to an imaging target, a slice direction gradient magnetic field waveform (Gss), a readout direction gradient magnetic field waveform (Gro), a phase encoding direction gradient magnetic field waveform (Gpe), and a deviation (Δf) of a carrier wave from a center frequency during the application of the radio-frequency pulse. A period P1 is a tag sequence part for labeling blood or cerebrospinal fluid. A period P2 is a main pulse sequence part for imaging. Although the fast spin echo method is employed in this example, it is possible to use any imaging method such as the coherent gradient echo method (the true SSFP method, true FISP or balanced FFE method).

As apparent from a comparison between FIGS. 5 and 24, the pulse sequence in the second embodiment has periods P1 and P2 similar to those in the pulse sequence disclosed in Japanese Patent Application KOKAI Publication No. 2001-252263, and further have a period P11 before period P1. Period P11 is a period for detecting a trigger starting period P1. Then, a time point in which the trigger is detected at period P11 is set as the reference time point so that the imaging cycle including labeling at period P1 and echo collection at period P2 is repeated a plurality of times.

Figure 6:
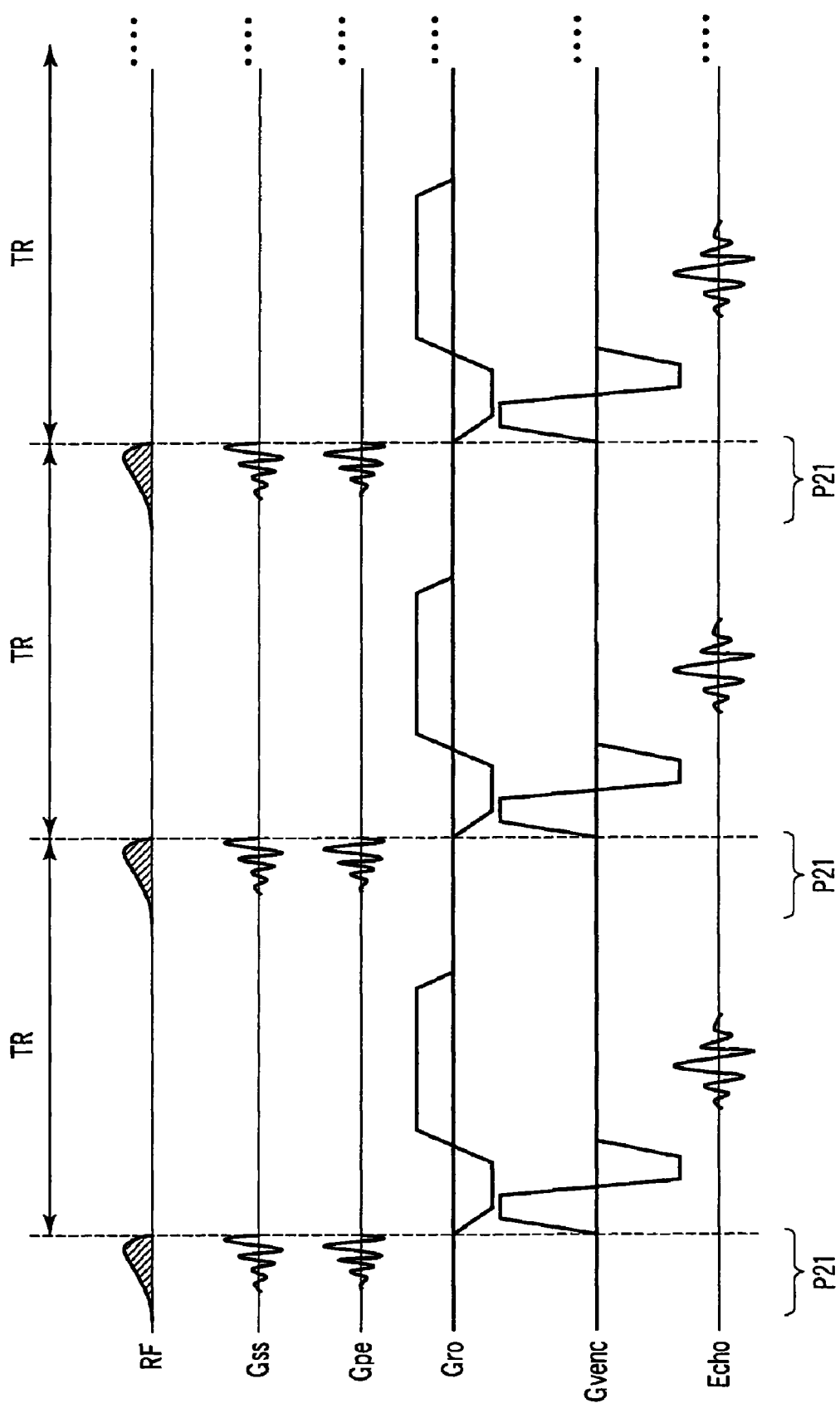
FIG. 6 is a diagram showing a pulse sequence for trigger detection in a period P11 in FIG. 5.

FIG. 6 is a diagram showing a pulse sequence for trigger detection in period P11 in FIG. 5. Waveforms shown in FIG. 6 represent, from top to bottom, a radio-frequency (RF) pulse applied to an imaging target, a slice direction gradient magnetic field waveform (Gss), a readout direction gradient magnetic field waveform (Gro), a phase encoding direction gradient magnetic field waveform (Gpe), a gradient magnetic field pulse (Gvenc) for flow encoding, and an echo signal waveform (Echo). A period P21 is a two-dimensional RF pulse for exciting a cylindrical region. The excitation by the two-dimensional RF pulse is known from Hardy, C. J., and Cline, H. E., 1989. "Broadband Nuclear Magnetic Resonance Pulses with Two-dimensional Spatial Selectivity," J. Appl. Phys 66:1513-1516.

In order to raise the time resolution of a flow velocity, the imaging region can be limited by a two-dimensional excitation method in the slice direction and phase encoding direction to measure a limited volume of cerebrospinal fluid or blood in one time TR. After the excitation, the gradient magnetic field pulse Gvenc for flow encoding is applied until the echo collection such that a phase variation proportionate to an average flow velocity during a period is produced in an echo signal. In addition, the time TR is, for example, about 10 to 200 ms.

Figure 7:
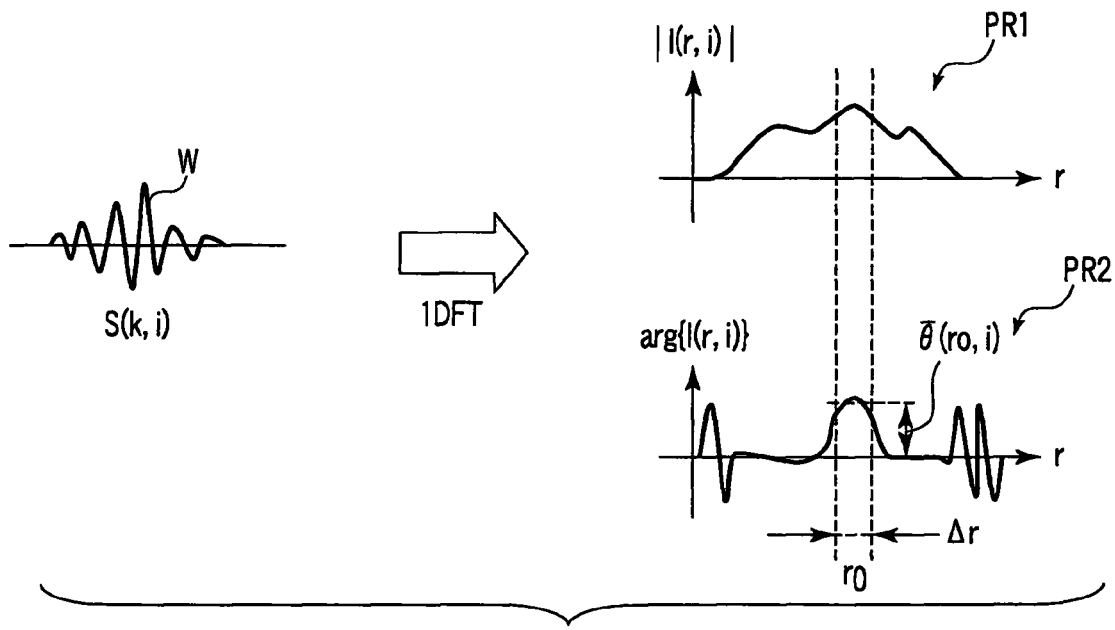
FIG. 7 is a diagram showing one example of a waveform of an echo signal obtained by the pulse sequence for trigger detection, and profiles of an absolute value and a phase in a readout direction obtained by one-dimensional Fourier transformation of the echo signal.

An echo signal having a waveform such as a waveform W shown in FIG. 7 can be obtained by the above-mentioned pulse sequence for trigger detection. Then, the echo signal is subjected to one-dimensional Fourier transformation (1DFT) by the host computer 6 such that profiles PR1 and PR2 of an absolute value and a phase in the readout direction are obtained as shown in FIG. 7.

Now, before starting imaging, set in accordance with an instruction of, for example, an operator are a region to be excited in the pulse sequence for trigger detection (hereinafter referred to as an excitation region) and a region targeted for the observation of a phase variation (hereinafter referred to as an observation region).

Figure 9:
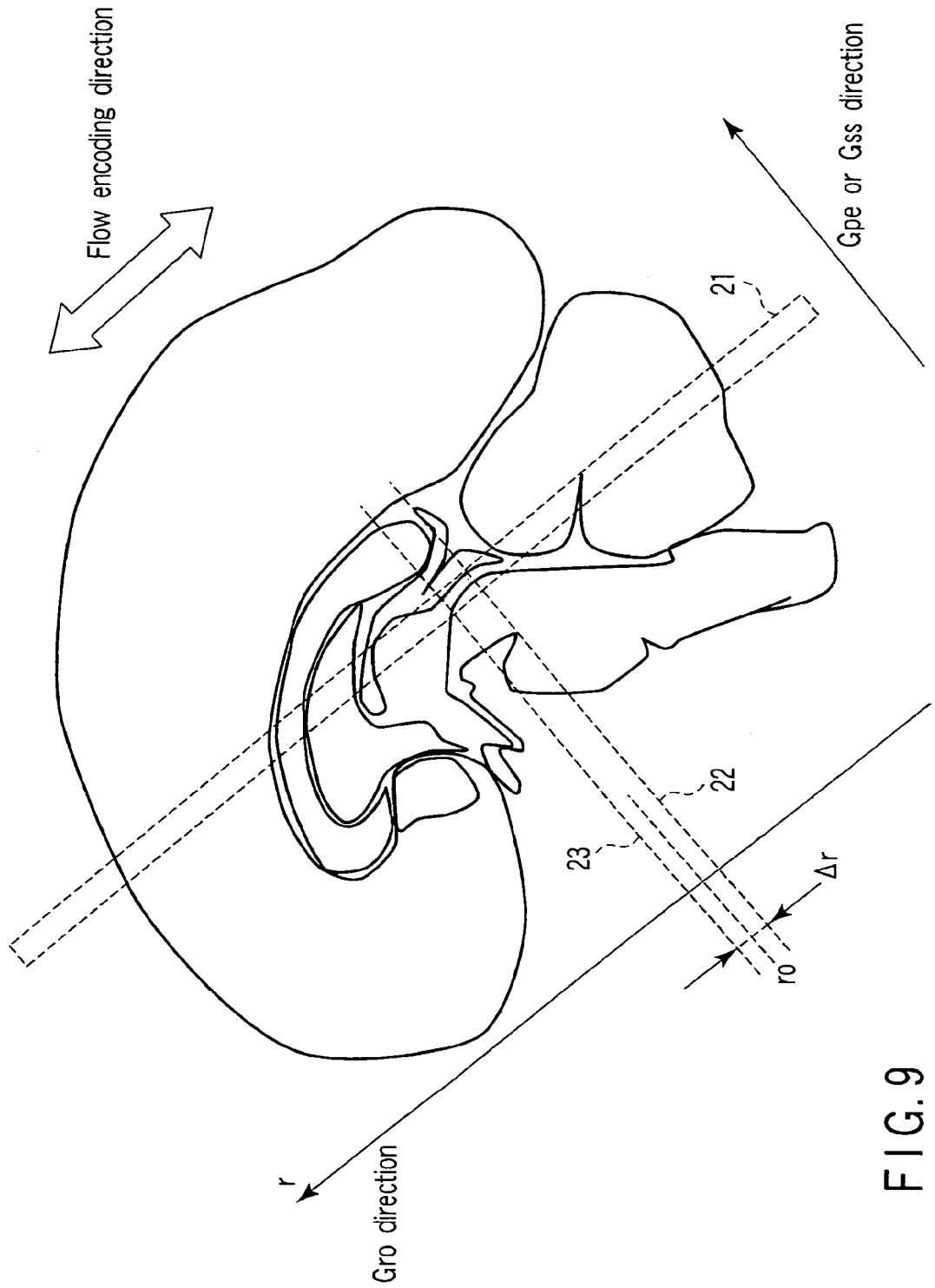
FIG. 9 is a diagram showing an example of how an excitation region and an observation region are set in the second embodiment.

FIG. 9 is a diagram showing an example of how the excitation region and the observation region are set. In this example, the operator indicates, on a positioning image, a rectangular frame 21 representing the excitation region and two straight lines 22 and 23 perpendicular to the readout direction. Then, the host computer 6 sets, as the excitation region, a columnar (bar-shaped) region whose projected shape looks like the rectangular frame 21. Further, the host computer 6 sets the observation region in accordance with an intermediate position $r_0$ in the readout direction of the straight lines 22 and 23 and a space Δr between the straight lines 22 and 23.

FIG. 10 is a diagram showing another example of how the excitation region and the observation region are set. In this example, since the readout direction is different from that in the example in FIG. 9, the directions of a rectangular frame 24 and straight lines 25 and 26 are different. However, no change is made in setting, as the excitation region, a columnar (bar-shaped) region whose projected shape looks like the rectangular frame 24 and in setting the observation region in accordance with the intermediate position $r_0$ in the readout direction of the straight lines 25 and 26 and the space Δr between the straight lines 25 and 26. In addition, the positions of the two straight lines in the readout direction may be used as information indicating the observation region instead of position $r_0$.

In addition, the positioning image in FIGS. 9 and 10 is a sagittal sectional image of a head. In this case, in the pulse sequence for trigger detection, changes in the flow velocity of the cerebrospinal fluid in the head are directly and continuously found by an NM signal to detect a trigger. In this case, as shown in FIGS. 9 and 10, it is desirable to set the excitation region so that the part of cerebral aqueduct with a high flow velocity and a great variation is included and to adjust a flow encoding direction to the flowing direction of the cerebrospinal fluid. Moreover, FIG. 9 shows an example in which the readout direction is set along the part of cerebral aqueduct, and FIG. 10 shows an example in which the slice direction or phase encoding direction is set along the part of cerebral aqueduct. The example in FIG. 10 has a smaller range in which the part of the cerebrospinal fluid to be observed is excited in the pulse sequence for trigger detection and, therefore, has an advantage that the main imaging executed after the trigger detection is less affected.

The host computer 6 measures an average phase variation $\theta(r_0, i)$ within the observation region in the phase profile PR2. Note that i indicates an index of the number of repetition of the time TR. The observation region is set as described above such that a target voxel can be smaller, the effect of a partial volume is less, and a phase variation faithfully reflecting the change of the flow velocity can be measured.

Figure 8:
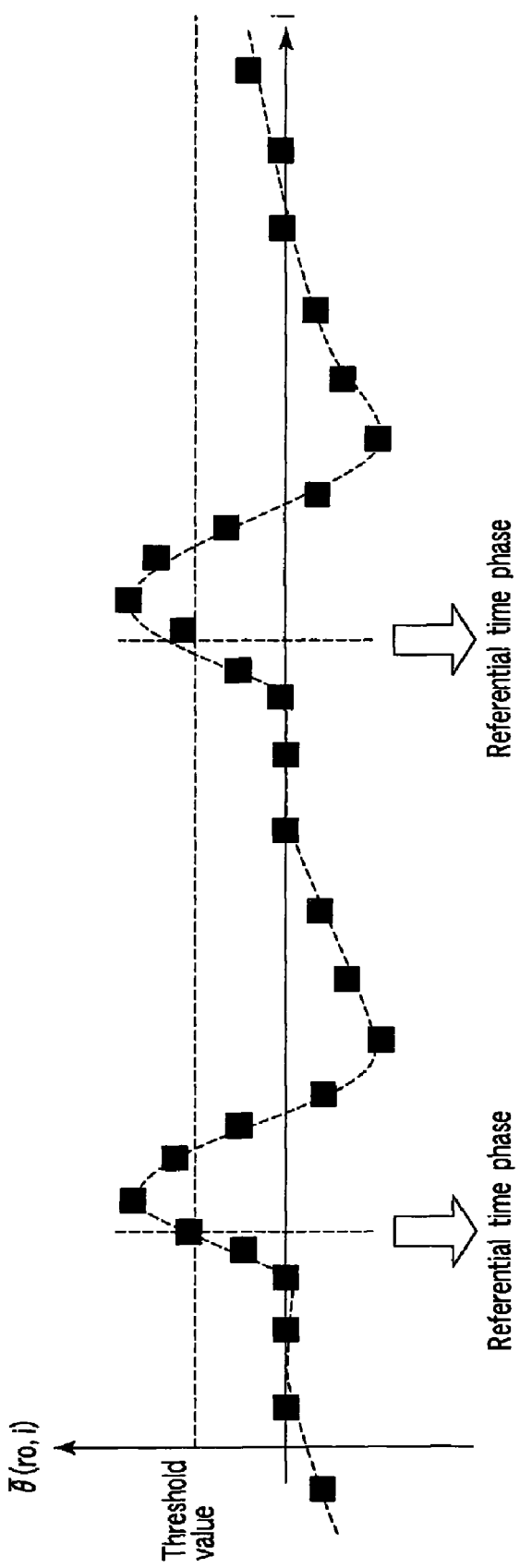
FIG. 8 is a diagram in which a phase change $\theta(ro, i)$ measured by the pulse sequence for trigger detection is plotted in order of time.

If the phase variation $\theta(r_0, i)$ measured at every the time TR is plotted in order of time, the pulsation of the cerebrospinal fluid is shown, for example, as in FIG. 8. Thus, a time point when the measured phase variation $\theta(r_0, i)$ coincides with a predetermined state is set as a reference time point such that this reference time point accurately synchronizes with the pulsation of the cerebrospinal fluid. FIG. 8 shows an example wherein a time point in which the phase variation $\theta(r_0, i)$ exceeds a threshold value is determined to be the reference time point. In order to determine the reference time point, it is also possible to employ other methods such as a method that temporally differentiates a waveform, for example, as shown in FIG. 8 to detect an inflection point. However, part of data can only be collected for the phase variation $\theta(r_0, i)$ after the start of imaging, and it is therefore necessary in some cases to sequentially execute the sequence for trigger detection before the start of imaging to determine the intervals of an average reference time point (trigger) or a threshold value that enables a stable detection of the reference time point (trigger).

Then, as shown in FIG. 5, the host computer 6 controls the sequencer 5 to repetitively perform the pulse sequence in periods P1 and P2, that is, the main imaging in synchronization with the reference time point determined in period P11 as described above. In addition, in the example in FIG. 5, the pulse sequence in period P1 is triggered upon reaching the reference time point.

Thus, according to the second embodiment, the pulsation of the cerebrospinal fluid is observed and the reference time point is determined on the basis of the result of the observation, such that it is possible to more accurately collect echoes synchronously with the pulsation of the cerebrospinal fluid than in the case where the ECG is used as the synchronization waveform. As a result, the influence of periodic changes with pulsation is held down and a change and artifact of the image in each imaging can be held down.

In addition, the pulse sequence for trigger detection in the second embodiment can be applied to the sequence for imaging in, for example, the first and third embodiments.

Part (e.g., one-dimensional Fourier transformation) of the processing for trigger detection may be carried out in the arithmetical unit 10.

While the example has been shown where a local change in the flow velocity of the cerebrospinal fluid is targeted for the trigger detection, it is known that cerebral parenchyma is moved by the pulsation of the cerebrospinal fluid. It is also possible to apply a high-intensity gradient magnetic field pulse (Gvenc) for flow encoding and target a slight motion in the part of cerebral parenchyma for the trigger detection. It is also possible to target a change in a blood flow for the trigger detection.

Third Embodiment

The third embodiment is described below. The third embodiment corresponds to Second Problem.

Figure 11:
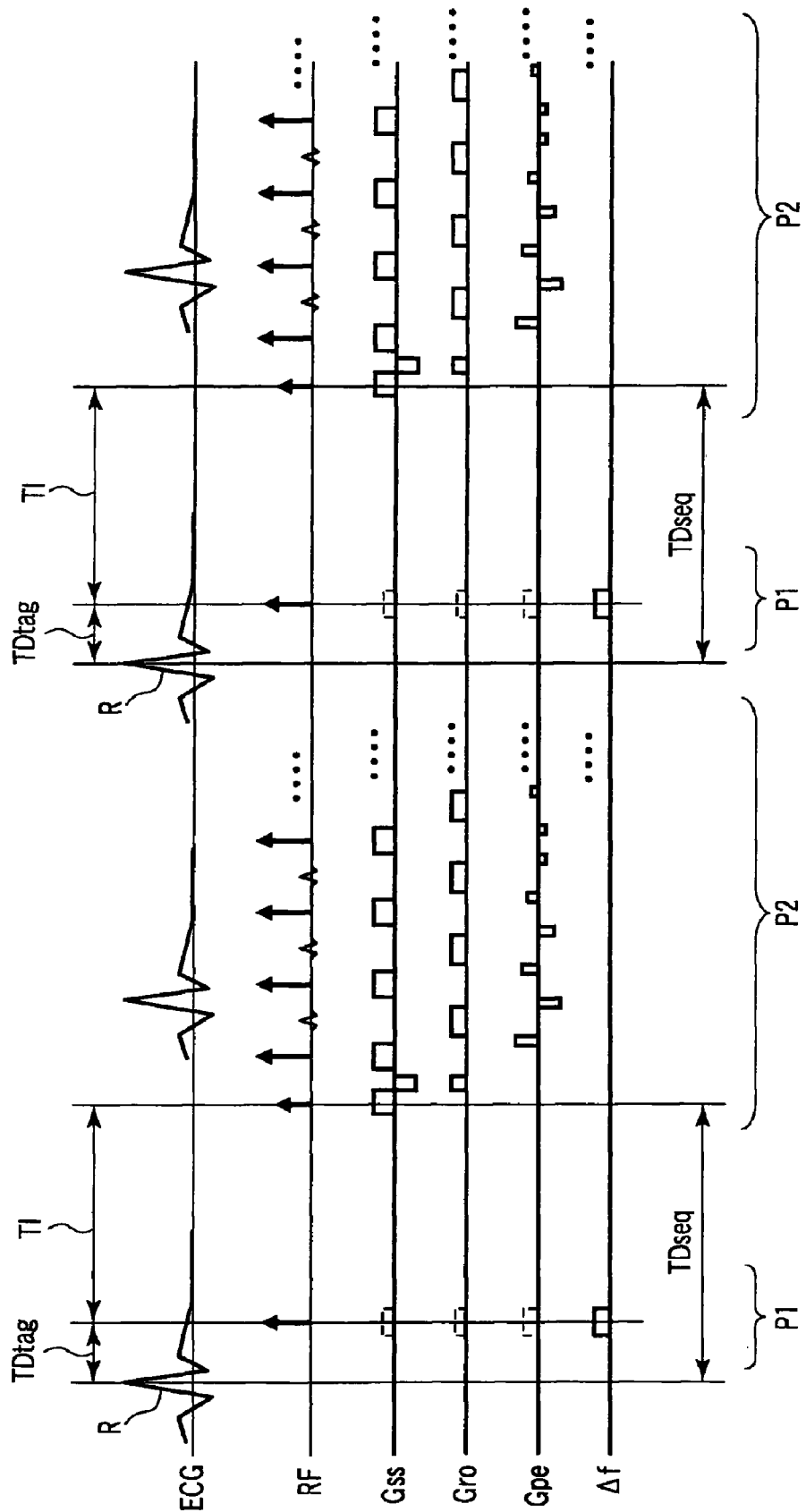
FIG. 11 is a diagram showing a pulse sequence in a third embodiment.

FIG. 11 is a diagram showing a pulse sequence in the third embodiment. Waveforms shown in FIG. 11 represent, from top to bottom, an electrocardiograph (ECG) as a synchronization waveform, a radio-frequency (RF) pulse applied to an imaging target, a slice direction gradient magnetic field waveform (Gss), a readout direction gradient magnetic field waveform (Gro), a phase encoding direction gradient magnetic field waveform (Gpe), and a deviation (Δf) of a carrier wave from a center frequency during the application of the radio-frequency pulse. A period P1 is a tag sequence part for labeling blood or cerebrospinal fluid. A period P2 is a main pulse sequence part for imaging. Although a fast spin echo method is employed in this example, it is possible to use any imaging method such as the coherent gradient echo method (the true SSFP method, true FISP or balanced FFE method).

As apparent from a comparison between FIGS. 11 and 24, the pulse sequence in the third embodiment is based on the pulse sequence disclosed in Japanese Patent Application KOKAI Publication No. 2001-252263. That is, an imaging cycle comprising labeling in period P1 and echo collection in period P2 is repeated a plurality of times. The pulse sequence in the third embodiment is different from the pulse sequence in FIG. 24 in which the time TDtag and the inversion time TI are constant in the respective cycles. In addition, Japanese Patent Application KOKAI Publication No. 2001-252263 also discloses a sequence in which the time TDtag and the inversion time TI are constant in the respective cycles, but a labeling region is also the same in the respective cycles in the third embodiment while the labeling region varies cycle by cycle in Japanese Patent Application KOKAI Publication No. 2001-252263. Such a pulse sequence can be produced by the control of the sequencer 5.

A plurality of images reconstructed on the basis of the echo data collected in every imaging cycle are sequentially displayed such that it is possible to only observe an image change due to a variation in the motion of an observation target during each imaging. The order of sequentially displayed images may be replaced as necessary depending on the distance at which a labeled portion is reached on each image.

Figure 12:
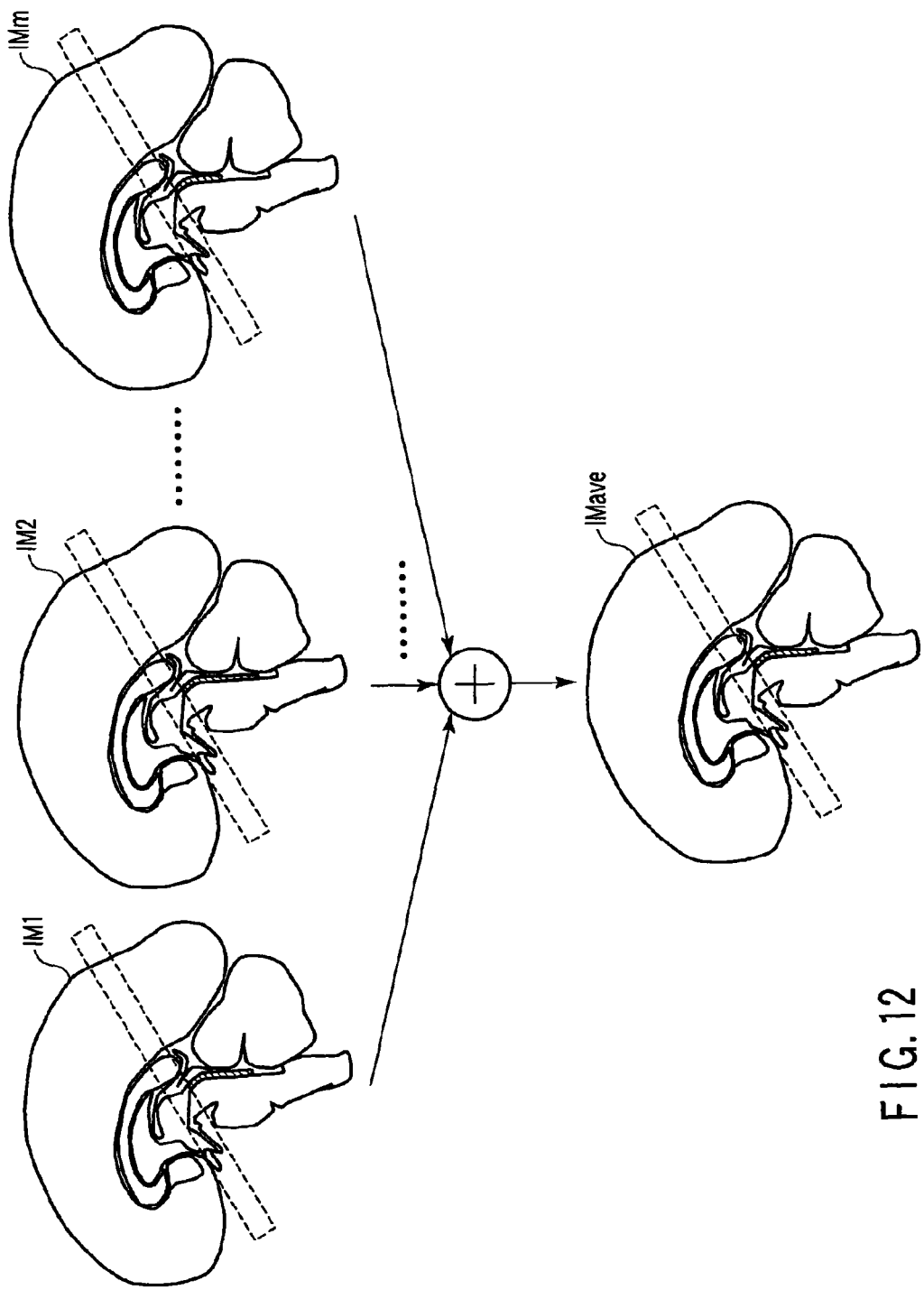
FIG. 12 is a diagram showing how images IM1, IM2, ..., IMm are averaged to generate an average image IMave.
Figure 13:
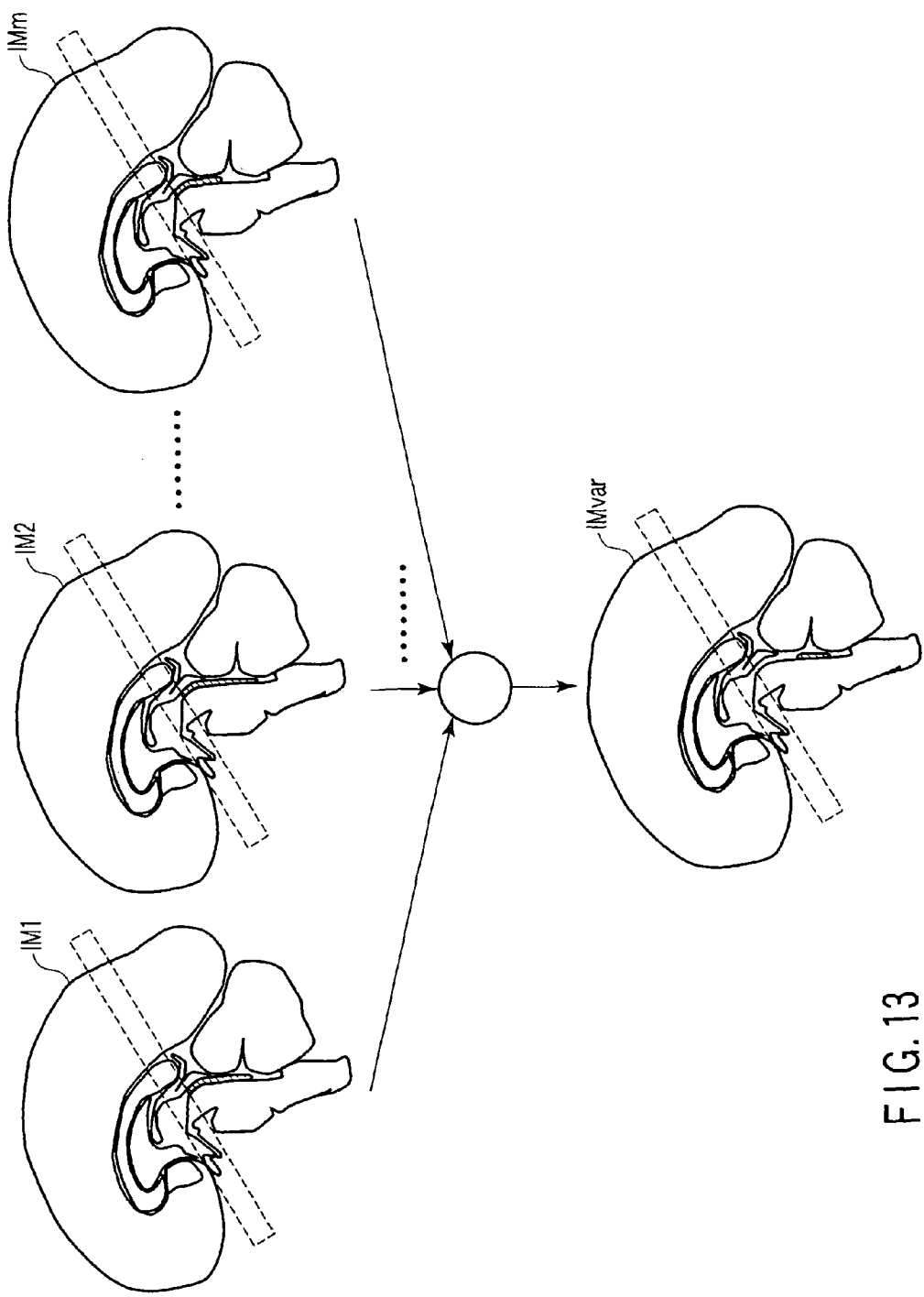
FIG. 13 is a diagram showing how to generate a variance image IMvar proportionate to the variance of the images IM1, IM2, ..., IMm.

Furthermore, in order to reduce the influence of each variation of the flow velocity, a plurality of taken images IM1, IM2, ..., IMm are averaged to generate and display an average image IMave, for example, as shown in FIG. 12. Alternatively, a variance image IMvar proportionate to the variance of the images IM1, IM2, ..., IMm may be generated and displayed, for example, as shown in FIG. 13. Moreover, the average image IMave and the variance image IMvar may be superposed on each other and displayed with different colors.

Furthermore, a plurality of image collections as described above are carried out in such a manner as to change the inversion time TI and the labeling region as necessary, and a plurality of images thus obtained are averaged, so that a series of such processing may be performed for each of the different inversion times TI and the labeling regions at different positions, and a plurality of obtained different images after averaging may be sequentially displayed. In this case, the influence of each variation of the flow velocity that has been evident in each imaging can be significantly reduced, and an image change due to the difference of the inversion times TI and the positions of the labeling regions can be more vividly displayed.

The various images as described above are displayed on the display 12 under the control of, for example, the host computer 6. Moreover, various kinds of image processing are carried out in the host computer 6 and the arithmetical unit 10.

Fourth Embodiment

The fourth embodiment is described below. The fourth embodiment corresponds to Third Problem.

Figure 14:
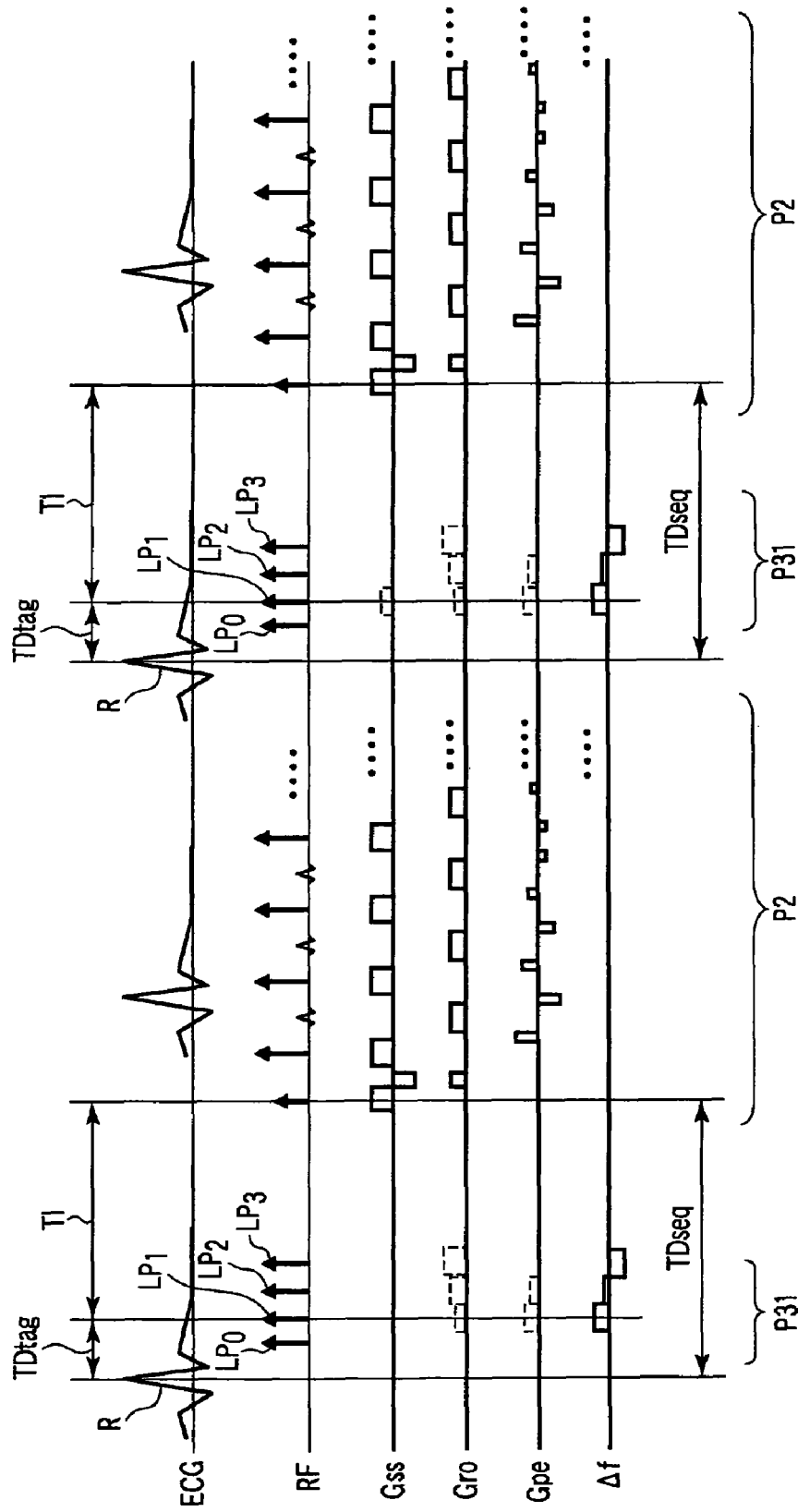
FIG. 14 is a diagram showing a pulse sequence in a fourth embodiment.

FIG. 14 is a diagram showing a pulse sequence in the fourth embodiment. Waveforms shown in FIG. 14 represent, from top to bottom, an electrocardiograph (ECG) as a synchronization waveform, a radio-frequency (RF) pulse applied to an imaging target, a slice direction gradient magnetic field waveform (Gss), a readout direction gradient magnetic field waveform (Gro), a phase encoding direction gradient magnetic field waveform (Gpe), and a deviation (Δf) of a carrier wave from a center frequency during the application of the radio-frequency pulse. A period P31 is a tag sequence part for labeling blood or cerebrospinal fluid. A period P2 is a main pulse sequence part for imaging. Although a fast spin echo method is employed in this example, it is possible to use any imaging method such as the coherent gradient echo method (the true SSFP method, true FISP or balanced FFE method).

In the pulse sequence in the fourth embodiment, an imaging cycle comprising labeling in period P31 and echo collection in period P2 is repeated a plurality of times. The pulse sequence for the echo collection in period P2 is similar to that shown in FIG. 24.

In period P31, three labeling pulses $LP_1$, $LP_2$ and $LP_3$ are sequentially applied from a time point when a time TDtag has passed from a reference time point in which an R wave is produced in the ECG. When labeling pulses $LP_1$ to $LP_3$ are applied, the gradient magnetic field waveform is varied as shown in FIG. 14 to vary the labeling region. Further, a labeling pulse $LP_0$ is applied before the application of labeling pulse $LP_1$. At this time, no gradient magnetic field is generated and the labeling region is nonselective. Such a pulse sequence can be produced by the control of the sequencer 5.

The region excited by any one of labeling pulses $LP_1$ to $LP_3$ is also inversely excited 180 degrees by labeling pulse $LP_0$. Since the time difference between labeling pulse $LP_0$ and labeling pulse $LP_1$, $LP_2$ or $LP_3$ is short enough for a T1 value of a labeling target such as the cerebrospinal fluid, the regions excited by labeling pulses $LP_1$ to $LP_3$ are in a condition similar to having been excited at a flip angle of 360 degrees, and the longitudinal magnetization is substantially in the initial state. On the other hand, the region that is not excited by any one of labeling pulses $LP_1$ to $LP_3$ is only excited by labeling pulse $LP_0$, and is, therefore, excited at 180 degrees, and the longitudinal magnetization is inverted.

Thus, according to the pulse sequence in the fourth embodiment, three different regions can be labeled. Further, labeled portions in the above-mentioned three regions alone show a high signal intensity in an image reconstructed from the echoes collected in period P2. That is, according to the image taken by the fourth embodiment, it is possible to know the dynamic state of the cerebrospinal fluid or blood in a wide range on one image and conduct an efficient inspection.

Furthermore, as the independent three regions can be labeled, it is possible to obtain an image effective in knowing the dynamic state of the cerebrospinal fluid or blood in different parts.

In addition, it is also possible to provide two labeling regions, or four or more labeling regions.

A specific example of how to set a plurality of labeling regions is described below.

Monro foramen, cerebral aqueduct and pontine cistern, foramen magnum, etc. are known to be clinically highly interested parts. In these parts, a portion in which the cerebrospinal fluid flows is narrow even in a normal healthy person, and a flow velocity is relatively high. In some cases, these parts become narrower than those of the normal healthy persons, or the flow of the cerebrospinal fluid changes. Therefore, as shown in, for example, FIG. 15, it is possible to designate, as labeling regions, a region R1 including Monro foramen, a region R2 including cerebral aqueduct and pontine cistern, and a region R3 including foramen magnum. The clinical knowledge of the circulatory pathways of the cerebrospinal fluid or blood is used to properly set the three labeling regions in this manner, such that it is possible to obtain an extremely useful image suitable to a clinical observation purpose.

Fossa lateralis cerebri is known to be another clinically highly interested part. When it is intended to know the dynamic state of the cerebrospinal fluid in fossa lateralis cerebri, it is desirable to set a section S1 that shows a sagittal image substantially closed to a coronal image and that passes in the vicinity of anterior commisure or optic chiasm, for example, as shown in FIG. 16. FIG. 17 is a diagram showing a two-dimensional (2D) image taken in section S1. Then, as shown in FIG. 17, labeling regions R11 and R12 are set on the two-dimensional image, and imaging is performed by the pulse sequence described above, such that, for example, an image as shown in FIG. 18 can be obtained. In portions with sufficiently less motion during imaging, labeling regions R11 and R12 during imaging as such show a high signal intensity. Due to the motion of the cerebrospinal fluid, the cerebrospinal fluid shows a high signal intensity in regions R13 to R17. This means that the cerebrospinal fluid is horizontally moving to and fro ("to-and-fro motion") in fossa lateralis cerebri. On the other hand, in general, a high signal intensity is rarely observed in regions R17 and R18. By making a comparison between the ranges of the high-signal-intensity parts, between right and left sides or between conditions before and after a treatment, diagnostically necessary information can be collected, so that it is useful to set a plurality of labeling regions such as labeling regions R11 and R12.

Fifth Embodiment

The fifth embodiment is described below. The fifth embodiment corresponds to Fourth Problem.

The host computer 6 displays an image, for example, as shown in FIG. 19 taken after labeling as a positioning image on the display 12, and instructed by an operator on the designation of a section on this image. In addition, in FIG. 19, a region 21 is designated as a labeling region, and a region 22 is visualized with a high signal intensity. Moreover, it is possible to apply any pulse sequence for taking the positioning image such as those shown in the embodiments described above or Japanese Patent Application KOKAI Publication No. 2001-252263.

Thus, the operator can decide an imaging section S11 including a portion with a high flow velocity of the cerebrospinal fluid, for example, as shown in FIG. 20.

FIG. 21 shows a two-dimensional image taken in imaging section S11. If such an image is taken after being provided with a labeling region R23 including Monro foramen as shown in FIG. 21, an image, for example, as shown in FIG. 22 can be obtained. A shaded region R24 is where the cerebrospinal fluid has moved from labeling region R23 after labeling, and shows a high signal intensity. That is, the image shown in FIG. 22 is taken by the pulse sequence that applies a nonselective IR pulse before a labeling pulse as shown in FIG. 4.

This permits a setting to be made after information on the flow of the cerebrospinal fluid has been known, so that it is possible to more easily set an imaging section in a part with a fast flow of the cerebrospinal fluid or in a diagnostically interested position or direction than when an imaging section is set with a normal positioning image.

Sixth Embodiment

The sixth embodiment is described below. The sixth embodiment corresponds to Fifth Problem.

Figure 23:
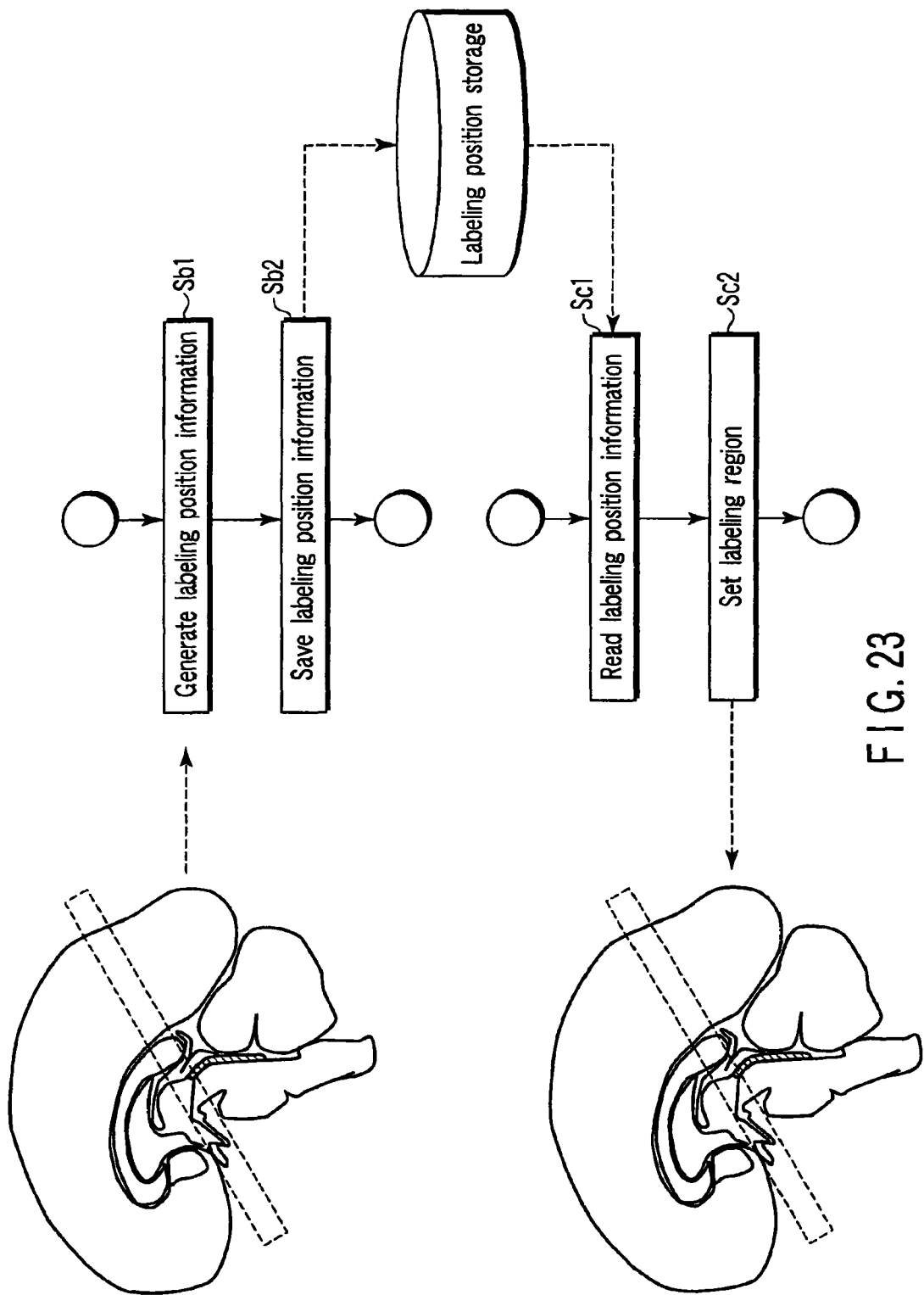
FIG. 23 is a flowchart for the characteristic processing of a host computer 6 in FIG. 1 in a sixth embodiment.

FIG. 23 is a flowchart for the characteristic processing of the host computer 6 in the sixth embodiment.

The host computer 6 is instructed on the designation of a labeling region as a preparation of an inspection. At this time, it is desirable to properly designate the labeling region in accordance with diagnostic purposes and other imaging conditions by taking advantage of clinical knowledge of the circulatory pathways of the cerebrospinal fluid or blood.

When the labeling region is designated, the host computer 6 generates labeling position information on the designated labeling region in step Sb1. The labeling position information includes information such as offset, rotation information, the width of the labeling region and the kind and duration of an RF pulse. In step Sb2, the host computer 6 saves the generated labeling position information in a labeling position storage.

As the labeling position storage, it is possible to use any storage medium such as the storage unit 11, a storage medium managed by an in-hospital server connected to the MRI apparatus 100 in the sixth embodiment via an in-hospital network, or a storage medium managed by a Web server connected to the MRI apparatus 100 in the sixth embodiment via, for example, the Internet.

During an actual inspection, the host computer 6 reads the labeling position information from the labeling position storage in step Sc1. Then, in step Sc2, the host computer 6 sets a labeling region on the basis of the labeling position information.

Thus, the labeling region can be easily and properly set during the actual inspection even by an operator of the apparatus who has no clinical knowledge of the circulatory pathways of the cerebrospinal fluid or blood, so that variations in image quality due to the level of skills of the operators of the apparatus can be reduced.

In addition, the labeling position information regarding several labeling regions may be saved in advance in the labeling position storage, and this labeling position information may be selectively read and used to set the labeling regions. This requires no designation of the labeling region as the preparation of the inspection and makes the operation simpler.

Various modifications such as those mentioned below can be made in the embodiments described above.

Other biological signals such as a sphygmographic signal can be used instead of the ECG or the signal indicating the pulsation of the cerebrospinal fluid.

A proper combination of the plurality of embodiments described above can be carried out.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A magnetic resonance imaging apparatus which generates a magnetic resonance image on the basis of an echo signal regarding a spin included in an imaging region of a subject, the apparatus comprising:
an imaging unit which applies a labeling pulse to invert the spin included in a labeling region within part of the imaging region and then applies an excitation pulse at a time point when an inversion time has passed from the application of the labeling pulse in order to collect the resulting echo signal; and
a control unit, the control unit controlling the imaging unit so that the echo signal in the imaging region is collected a plurality of times with variations in the inversion time, the control unit also controlling the imaging unit so that a time ranging from a reference time point within a biological signal obtained from the subject to the application of the excitation pulse is constant regardless of the inversion time in the plurality of collections of the echo signal.

2. A magnetic resonance imaging apparatus comprising:
an acquisition unit which acquires an echo signal regarding a spin included in an imaging region of a subject in accordance with a predetermined pulse sequence;
a reconstruction unit which reconstructs an image of the inside of the imaging region in accordance with the acquired echo signal;
a labeling unit which inverts the spin included in a labeling region within part of the imaging region to conduct labeling; and
a control unit, the control unit controlling the labeling unit and the acquisition unit so that a cycle of conducting the labeling and acquiring the echo signal from a time point when a given first time has passed from a time point of the labeling is carried out a plurality of times without changing the labeling region, the control unit also controlling the labeling unit and the acquisition unit so that each of the plurality of cycles is started at a time point when a given second time has passed from a periodic reference time point.

3. The magnetic resonance imaging apparatus according to claim 2, further comprising: a unit which generates a composite image of at least two of images reconstructed by the reconstruction unit on the basis of the echo signal acquired in each of the plurality of cycles.

4. The magnetic resonance imaging apparatus according to claim 2, further comprising: a unit which calculates the moving distance of the labeled spin on the basis of at least two images of interest out of images reconstructed by the reconstruction unit in accordance with the echo signal acquired in each of the plurality of cycles, and sequentially displays the images of interest in an order corresponding to the calculated moving distance.

5. The magnetic resonance imaging apparatus according to claim 2, wherein the control unit decides the reference time point on the basis of a synchronization signal.

6. The magnetic resonance imaging apparatus according to claim 5, wherein the control unit uses an electrocardiographic signal regarding the subject as the synchronization signal.

7. A magnetic resonance imaging apparatus comprising:
an acquisition unit which acquires an echo signal regarding a spin included in an imaging region of a subject in accordance with a predetermined pulse sequence;
a reconstruction unit which reconstructs an image of the inside of the imaging region in accordance with the acquired echo signal;
a labeling unit which inverts the spin included in a labeling region within part of the imaging region to conduct labeling;
an observation unit which repetitively acquires a magnetic resonance signal from within the labeling region and observes a change of the flow velocity of a fluid in the labeling region on the basis of a change of the repetitively acquired magnetic resonance signal; and
a control unit, the control unit controlling the labeling unit and the acquisition unit so that a cycle of conducting the labeling and acquiring the echo signal from a time point when a predetermined first time has passed after the labeling is carried out a plurality of times, the control unit also controlling the labeling unit and the acquisition unit so that the cycle is started at a time point when a predetermined second time has passed from a reference time point at which the observed change of the flow velocity coincides with a predetermined state.

8. The magnetic resonance imaging apparatus according to claim 7, wherein the observation unit only acquires the magnetic resonance signal from an observation region within part of the labeling region.

9. The magnetic resonance imaging apparatus according to claim 7, wherein the observation region is a cerebral aqueduct.

10. A magnetic resonance imaging apparatus comprising:
an acquisition unit which acquires an echo signal regarding a spin included in an imaging region of a subject in accordance with a predetermined pulse sequence;
a reconstruction unit which reconstructs an image of the inside of the imaging region in accordance with the acquired echo signal;
a labeling unit which inverts the spin included in the imaging region and then inverts the spin included in each of a plurality of labeling regions within part of the imaging region to conduct labeling; and
a control unit, the control unit controlling the labeling unit and the acquisition unit so that a cycle of conducting the labeling and acquiring the echo signal from a time point when a predetermined first time has passed from a time point of the labeling is carried out a plurality of times, the control unit also controlling the labeling unit and the acquisition unit so that the cycle is started at a time point when a predetermined second time has passed from a periodic reference time point.

11. A magnetic resonance imaging apparatus comprising:
an acquisition unit which acquires an echo signal regarding a spin included in an imaging region of a subject in accordance with a predetermined pulse sequence;
a reconstruction unit which reconstructs an image of the inside of the imaging region in accordance with the acquired echo signal;
a labeling unit which inverts the spin included in a labeling region within part of the imaging region to conduct labeling;
a control unit, the control unit controlling the labeling unit and the acquisition unit so that a cycle of conducting the labeling and acquiring the echo signal from a time point when a predetermined first time has passed after the labeling is carried out a plurality of times, the control unit also controlling the labeling unit and the acquisition unit so that each of the plurality of cycles is started at a time point when a predetermined second time has passed from a periodic reference time point;
a unit which displays, as a positioning image, one of the plurality of images reconstructed on the basis of the echo signal acquired in each of the plurality of cycles; and
a unit which accepts a designation of an imaging section on the positioning image.

12. A magnetic resonance imaging apparatus having access to a storage device, the apparatus comprising:
an acquisition unit which acquires an echo signal regarding a spin included in an imaging region of a subject in accordance with a predetermined pulse sequence;
a reconstruction unit which reconstructs an image of the inside of the imaging region in accordance with the acquired echo signal;
a labeling unit which inverts the spin included in a labeling region within part of the imaging region to conduct labeling;
a control unit, the control unit controlling the labeling unit and the acquisition unit so that a cycle of conducting the labeling and acquiring the echo signal from a time point when a predetermined first time has passed after the labeling is carried out a plurality of times, the control unit also controlling the labeling unit and the acquisition unit so that each of the plurality of cycles is started at a time point when a predetermined second time has passed from a periodic reference time point; and
a unit which sets the labeling region on the basis of information stored in the storage device.

13. The magnetic resonance imaging apparatus according to claim 12, including the storage device therein.

14. The magnetic resonance imaging apparatus according to claim 12, further comprising: a unit which saves, in the storage device, information indicating the labeling region set on the basis of an instruction of a user.

15. A magnetic resonance imaging method which generates a magnetic resonance image on the basis of an echo signal regarding a spin included in an imaging region of a subject, the method comprising:
applying a labeling pulse to invert the spin included in a labeling region within part of the imaging region and then applying an excitation pulse at a time point when an inversion time has passed from the application of the labeling pulse in order to collect the resulting echo signal; and
controlling the application of the labeling pulse and the collection so that the echo signal in the imaging region is collected a plurality of times with variations in the inversion time, and also controlling the application of the labeling pulse and the collection so that a time ranging from a reference time point within a biological signal obtained from the subject to the application of the excitation pulse is constant regardless of the inversion time in the plurality of collections of the echo signal.

16. A magnetic resonance imaging method comprising:

acquiring an echo signal regarding a spin included in an imaging region of a subject in accordance with a predetermined pulse sequence;

inverting the spin included in a labeling region within part of the imaging region to conduct labeling;

controlling the labeling and the acquisition so that a cycle of conducting the labeling and acquiring the echo signal from a time point when a given first time has passed from a time point of the labeling is carried out a plurality of times without changing the labeling region, and also controlling the labeling and the acquisition so that each of the plurality of cycles is started at a time point when a given second time has passed from a periodic reference time point; and reconstructing an image of the inside of the imaging region in accordance with the acquired echo signal.

17. A magnetic resonance imaging method comprising:

acquiring an echo signal regarding a spin included in an imaging region of a subject in accordance with a predetermined pulse sequence;

inverting the spin included in a labeling region within part of the imaging region to conduct labeling;

repetitively acquiring a magnetic resonance signal from within the labeling region and observing a change of the flow velocity of a fluid in the labeling region on the basis of a change of the repetitively acquired magnetic resonance signal;

controlling the labeling and the acquisition so that a cycle of conducting the labeling and acquiring the echo signal from a time point when a predetermined first time has passed after the labeling is carried out a plurality of times, and also controlling the labeling and the acquisition so that the cycle is started at a time point when a predetermined second time has passed from a reference time point at which the observed change of the flow velocity coincides with a predetermined state; and reconstructing an image of the inside of the imaging region in accordance with the acquired echo signal.

18. A magnetic resonance imaging method comprising:

acquiring an echo signal regarding a spin included in an imaging region of a subject in accordance with a predetermined pulse sequence;

inverting the spin included in the imaging region and then inverting the spin included in each of a plurality of labeling regions within part of the imaging region to conduct labeling; and controlling the labeling and the acquisition so that a cycle of conducting the labeling and acquiring the echo signal from a time point when a predetermined first time has passed from a time point of the labeling is carried out a plurality of times, and also controlling the labeling and the acquisition so that the cycle is started at a time point when a predetermined second time has passed from a periodic reference time point;

reconstructing an image of the inside of the imaging region in accordance with the acquired echo signal.

19. A magnetic resonance imaging method comprising:

acquiring an echo signal regarding a spin included in an imaging region of a subject in accordance with a predetermined pulse sequence;

inverting the spin included in a labeling region within part of the imaging region to conduct labeling;

controlling the labeling and the acquisition so that a cycle of conducting the labeling and acquiring the echo signal from a time point when a predetermined first time has passed after the labeling is carried out a plurality of times, and also controlling the labeling and the acquisition so that each of the plurality of cycles is started at a time point when a predetermined second time has passed from a periodic reference time point;

reconstructing an image of the inside of the imaging region in accordance with the acquired echo signal;

displaying, as a positioning image, one of the plurality of images reconstructed on the basis of the echo signal acquired in each of the plurality of cycles; and accepting a designation of an imaging section on the positioning image.

20. A magnetic resonance imaging method in a magnetic resonance imaging apparatus having access to a storage device, the method comprising:

acquiring an echo signal regarding a spin included in an imaging region of a subject in accordance with a predetermined pulse sequence;

inverting the spin included in a labeling region within part of the imaging region to conduct labeling;

controlling the labeling and the acquisition so that a cycle of conducting the labeling and acquiring the echo signal from a time point when a predetermined first time has passed from a time point of the labeling is carried out a plurality of times, and also controlling the labeling and the acquisition so that each of the plurality of cycles is started at a time point when a predetermined second time has passed from a periodic reference time point;

setting the labeling region on the basis of information stored in the storage device; and reconstructing an image of the inside of the imaging region in accordance with the acquired echo signal.

* * * * *